US009566254B2

(12) United States Patent
Allen, III et al.

(10) Patent No.: US 9,566,254 B2

(45) Date of Patent: Feb. 14, 2017

(54) INHIBITORS AND METHODS OF INHIBITING BACTERIAL AND VIRAL PATHOGENS

(71) Applicant: SIGA TECHNOLOGIES, INC., Corvallis, OR (US)

(72) Inventors: Robert D. Allen, III, Corvallis, OR (US); Sean M. Amberg, Corvallis, OR (US); Dongcheng Dai, Corvallis, OR (US); James R. Burgeson, Albany, OR (US); Dennis E. Hruby, Albany, OR (US)

(73) Assignee: SIGA TECHNOLOGIES, INC., Corvallis, OR (US)

( * ) Notice: Subject to any disclaimer, the term of this patent is extended or adjusted under 35 U.S.C. 154(b) by 0 days.

(21) Appl. No.: 14/955,697

(22) Filed: Dec. 1, 2015

(65) Prior Publication Data

US 2016/0081950 A1 Mar. 24, 2016

Related U.S. Application Data

(62) Division of application No. 13/578,413, filed as application No. PCT/US2011/025356 on Feb. 18, 2011, now Pat. No. 9,233,087.

(60) Provisional application No. 61/306,102, filed on Feb. 19, 2010.

(51) Int. Cl.

| | |
|---|---|
| ***A61K 31/17*** | (2006.01) |
| ***A61K 31/4409*** | (2006.01) |
| ***C07C 335/20*** | (2006.01) |
| ***C07C 335/26*** | (2006.01) |
| ***C07C 335/38*** | (2006.01) |
| ***A61K 45/06*** | (2006.01) |
| ***C07D 213/81*** | (2006.01) |
| ***C07D 213/82*** | (2006.01) |
| ***C07D 495/04*** | (2006.01) |
| ***A61K 31/675*** | (2006.01) |
| ***A61K 31/7056*** | (2006.01) |
| ***A61K 38/21*** | (2006.01) |
| ***A61K 47/48*** | (2006.01) |

(52) U.S. Cl.

CPC ........... *A61K 31/17* (2013.01); *A61K 31/4409* (2013.01); *A61K 31/675* (2013.01); *A61K 31/7056* (2013.01); *A61K 38/21* (2013.01); *A61K 45/06* (2013.01); *A61K 47/48215* (2013.01); *C07C 335/20* (2013.01); *C07C 335/26* (2013.01); *C07C 335/38* (2013.01); *C07D 213/81* (2013.01); *C07D 213/82* (2013.01); *C07D 495/04* (2013.01); *Y10S 514/888* (2013.01)

(58) Field of Classification Search

None

See application file for complete search history.

(56) References Cited

U.S. PATENT DOCUMENTS

2008/0207760 A1 8/2008 Huang

FOREIGN PATENT DOCUMENTS

| | | |
|---|---|---|
| EP | 2279750 | 2/2011 |
| EP | 2583962 | 4/2013 |
| WO | WO2008-029096 | 3/2000 |
| WO | 2007/120374 | 10/2007 |
| WO | 2009-119167 | 10/2009 |

OTHER PUBLICATIONS

Benzamide, 2-chloro-N-[3-[[[[4-(,1 -dimethykethyl)benzoyl]amino]thioxomethyl]amino]phely] Database Registry (Online), Chemical Abstracts Service, Aug. 9, 2012, Columbus, Ohio.

Benzamide, 4-(1,1-dimethylethyl-N-[[(4-nitrophenyl)amino]thuixomethyl] Database Registry (Online), Chemical Abstracts Service, Sep. 12, 2001, Columbus, Ohio.

European Search Report from European Application No. 14194598.0, dated Mar. 23, 2015.

Kee, et al., Nonsubstiate Based Inhibitors of Dengue Virus Serino Protease: A Molecular Docking Approach to Study Binding Interactions between Protease and Inhibitors, Asia Pacific, Journal of Molecular Biology and Biotechnology, vol. 15(2), pp. 53-59, 2007, Abstract, p. 53-p. 57.

Karakus, et al., Synthesis, antiviral and anticancer activity of some novel thioureas derived from N-(4-nitro-2-phenoxyphenyl)-methanesulfonamide, European Journal of Medicinal Chemistry 44, pp. 3591-3595, 2009, p. 3592-Scheme 1, Table 1, p. 3593.

Saeed, et al., Synthesis Characterization and Antibbacterial Activity of some 1-Aroyl-3-Aryl Thioureas, Chemistry, vol. 18(5), pp. 152-158, 2009, Abstract, p. 154.

International Search Report Application No. PCT/US2011/25356, Dated May 26, 2011.

Written Opinion of the International Searching Authority issued in Application No. PCT/US2011/25356, Dated May 26, 2011.

Lain et al., “Discovery, In Vivo Activity, and Mechanism of Action of a Small-Molecule p54 Activator”, Cancer Cell, vol. 13 (2008), pp. 454-463.

National Institute of Allergy and Infectious Diseases (NIAID), “Understanding Microbes in Sickness and in Health”, NIH Publication No. 06-4914, Jan. 2006, pp. 1-52.

Rappé et al., Annual Review of Microbiology, 2003, vol. 57, pp. 369-394.

Pytela, et al., Chemometrical Analysis of Substituent Effects on 13C and 15N NMR Chemical Shifts in 1-Aroyl-3-Substituted Thioureas, Collect. Czech. Chem. Commun., vol. 54, Jan. 15, 1989, pp. 2399-2407.

European Search Report Application No. 11745286.2, Dated Nov. 10, 2013.

*Primary Examiner* — Savitha Rao
*Assistant Examiner* — Gregg Polansky
(74) *Attorney, Agent, or Firm* — Charles C. Achkar; Ostrolenk Faber LLP

(57) ABSTRACT

Compounds, pharmaceutical compositions and methods for treating viral and bacterial infections, by administering certain thiourea compounds, specifically acylthiourea, carboximidoylthiourea and S-alkyl isothiourea derivatives and analogs, in therapeutically effective amounts are disclosed.

33 Claims, No Drawings

INHIBITORS AND METHODS OF INHIBITING BACTERIAL AND VIRAL PATHOGENS

CROSS REFERENCE TO RELATED APPLICATIONS

This application is a divisional of U.S. Application No. 13/578,413 filed Sep. 5, 2012, which is a § 371 National Phase application based on PCT/US2011/025356 filed Feb. 18, 2011, which claims the benefit of U.S. Provisional Application No. 61/306,102 filed Feb. 19, 2010, the subject matter of each of which is incorporated by reference in its entirety.

STATEMENT REGARDING FEDERALLY SPONSORED RESEARCH OR DEVELOPMENT

The research described herein was supported in part by funds from the U.S. Government Department of Defense contract HDTRA1-10-C-0036 and the U.S. Government may therefore have certain rights in the invention.

FIELD OF THE INVENTION

This invention relates to certain thiourea compounds, specifically acylthiourea, carboximidoylthiourea and S-alkyl isothiourea derivatives and analogs. This invention also relates to the use of these certain thiourea derivatives and analogs, as well as compositions containing the same, for the treatment or prophylaxis of viral and bacterial infections as well as diseases associated thereof.

BACKGROUND OF THE INVENTION

Flaviviridae

Dengue is a member of the Flaviviridae family which are enveloped, positive-sense RNA viruses whose human pathogens also include West Nile virus (WNV), yellow fever virus (YFV), Japanese encephalitis virus (JEV), and tick-borne encephalitis virus (TBEV) among others. Dengue transmission is through the bite of an infected *Aedes aegypti* mosquito that is found in tropical and sub-tropical regions around the world. Dengue fever (DF) is an acute febrile disease caused by one of four closely related virus serotypes (DEN-1, DEN-2, DEN-3, and DEN-4). Dengue fever is classified based on its clinical characteristics into classical dengue fever, or the more severe forms, dengue hemorrhagic fever syndrome (DHF), and dengue shock syndrome (DSS). Recovery from infection from one serotype produces life-long immunity to that particular serotype, but provides only short-lived and limited protection against any of the other serotypes.

Each year regional epidemics of dengue cause significant morbidity and mortality, social disruption and substantial economic burden on the societies affected both in terms of hospitalization and mosquito control. Dengue is considered by the World Health Organization (WHO) to be the most important arthropod-borne viral disease with an estimated 50 million cases of dengue infection, including 500,000 DHF cases and 24,000 deaths worldwide each year (36, 37). Dengue is also a CDC and NIAID Category A pathogen and in terms of bio-defense, represents a significant threat to United States troops overseas. Preparedness for both biodefense and for the public health challenges posed by dengue will require the development of new vaccines and antiviral therapeutics.

Orthomyxoviridae

The influenza virus is a member of the Orthomyxoviridae family. Each year regional epidemics of influenza cause significant morbidity and mortality, social disruption and substantial economic burden. During "flu season" it is estimated that influenza infects 10-20% of the US population resulting in over 100,000 hospitalizations and 20,000 to 40,000 deaths. The economic impact caused by influenza due to decreased productivity and increased health care utilization is estimated to be in the billions of dollars.

Recent emergence of highly pathogenic avian influenza (H5N1) has elevated our fears of a possible human pandemic. The current circulating H5N1 strain of virus is unusually pathogenic in birds causing destruction of domestic and wild bird populations. In rare instances, the virus has infected humans causing mortality in almost 50% of cases. Should this virus acquire genetic traits that increase person to person transmissibility widespread adverse public health and economic outcomes would be expected. FDA-approved antiviral drugs are currently in use, but increasing resistance to existing countermeasures necessitates the development of new antiviral therapeutics with novel mechanisms of action against influenza.

Poxviridae

Orthopoxviruses are members of the Poxviridae family. Human orthopoxviruses cause a spectrum of diseases ranging from severe disseminated lesional disease characteristic of the most common type of variola virus infection (variola major) to localized lesional infection caused by vaccinia virus. Of the several species of orthopoxvirus known to infect humans, variola virus, the etiological agent of smallpox, causes far more serious infections than the other species of poxviruses. While variola virus no longer exists in the environment, other orthopoxviruses continue to circulate and cause disease. Monkeypox virus, which is endemic in some areas of the Democratic Republic of the Congo, causes a zoonotic disease that is characterized by a generalized infection resembling a milder version of smallpox. Vaccinia-like viruses have been isolated from patients in Brazil presenting with localized lesions of the hands and arms and cowpox virus infections are increasing in certain parts of Europe. These viruses are believed to be maintained in the population through rodent reservoirs and zoonotic disease is thought to arise from contact with infected animals, or through an intermediate species such as cattle or domestic pets. Disease severity in all cases is influenced by the status of the host immune system, with individuals suffering from certain skin disorders or who are immunocompromised developing the most severe infections. Preparedness for both biodefense and for the public health challenges posed by human orthopoxviruses requires the development of new antiviral therapeutics.

Togaviridae

Alphaviruses are members of the Togaviridae family. Alphaviruses cause a spectrum of human disease ranging from asymptomatic infection to severe encephalitis and death. The virus is transmitted by mosquito and is maintained in the environment through an enzootic cycle involving infection of sylvatic hosts. Some alphaviruses achieve further amplification by exploiting domestic animals such as equines and pigs. Interest in alphaviruses has been renewed, because of reports that certain species of alphaviruses have been developed into efficient, stable biological weapons that are infectious by aerosol delivery and easily produced in large quantities. No licensed vaccine or therapeutic exists to treat or prevent infection of pathogenic alphaviruses. Moreover, the antigenic diversity of this group of viruses presents a formidable challenge for vaccine development. Thus, therapeutics that target conserved replication functions of the virus serve as useful countermeasures for treatment of alphavirus disease.

Bunyaviridae

Based on recommendations by the CDC and the NIAID, viruses that might be used as biological weapons have been separated into three categories. Category A viruses are considered the most serious threat to national security. These viruses have the greatest potential to cause widespread illness and death in human populations. Category B viruses are considered biothreats due to the potential for weaponization of these pathogens, and the projected high morbidity and mortality rates that would accompany their use as aerosolized agents. Category C viruses include emerging pathogens with the potential to be developed as biowarfare agents or to otherwise pose a risk to public health and safety. A national research and development effort has been undertaken to develop a comprehensive biodefense strategy against these agents. Of note is the presence of four different members of the family Bunyaviridae among the viruses characterized as biothreats to the United States. This fact reflects the diverse worldwide impact of bunyavirus infections on populations of livestock and humans. RVFV, a Category A bunyavirus, has been the cause of massive agricultural and social hardship in Egypt and the Arabian peninsula. Infections of as many as 200,000 people have been estimated in two epizootic epidemics resulting from RVFV transmission in 1977 and 1978, with an estimated 600 associated fatalities. The second of the Category A bunyaviruses, hantavirus, has been the recognized cause of significant morbidity and mortality among military and civilian populations for over fifty years. U.S. troops suffered from chronic exposure to endemic hantavirus during the Korean conflict, and, more recently, hantavirus transmission from rodent vectors to human populations has resulted in outbreaks of human disease and death in the American southwest. CCHF, a Category C pathogen, is a virus transmitted to humans who work in close contact with livestock in geographic regions that extend from sub-Saharan Africa to northern China. Infection with CCHF can lead to death in as many as 30% of diagnosed individuals. CCHF has all of the characteristics of the Category A viruses, except that current cell culture systems limit large-scale production capabilities; any technological advances in this area would elevate the risk posed by CCHF. The category B bunyavirus, La Crosse encephalitis virus, is the leading cause of pediatric encephalitis in endemic regions of the) United States. To date, there are no specific vaccines or antivirals approved for the treatment of the Category A, B, or C bunyavirus infections in humans.

Arenaviridae

The arenaviruses are a diverse family of enveloped RNA viruses found worldwide. These viruses generate high morbidity and mortality and can be highly infectious by aerosol dissemination, promoting concern over their weaponization. Arenavirus infection in humans can lead to viral hemorrhagic fever, a serious illness characterized by extensive vascular damage and bleeding diathesis, fever, and multiple organ involvement. Arenavirus infection in rodents, the natural host animal, is usually chronic and asymptomatic. Five distinct arenaviruses cause severe HF in humans and are classified as category A pathogens, defined as those pathogens posing the greatest threat to public health and safety. These are Lassa fever, Machupo (causative agent of Bolivian HF), Junin (Argentine HF), Guanarito (Venezuelan HF), and Sabia, (Brazilian HF) viruses. Lassa fever is the most prominent biodefense target in this group, due to its current prevalence (estimated at up to a half-million cases annually, primarily in West Africa) and history of weaponization research. Junin and Machupo viruses (endemic in South America) were also reportedly pursued as biological weapons by the former Soviet Union. Preparedness for both biodefense and for the public health challenges posed by human arenaviruses requires the development of new antiviral therapeutics.

Filoviridae

Filoviruses including Ebola and Marburg viruses cause severe hemorrhagic disease in humans resulting in high mortality. Infections result from zoonotic transmission from an infected animal to humans. The natural reservoirs and routes of transmission are not fully understood. Person-to-person transmission occurs primarily through physical contact with infected material. No licensed vaccine or therapeutic exists to treat or prevent infection of filoviruses. Thus, therapeutics that target virus replication would serve as useful countermeasures for treatment of filovirus disease.

Retroviridae

The HIV virus is a member if the retrovirus family. Currently, over 42 million people are living with HIV/AIDS worldwide, and 74 percent of these infected people live in sub-Saharan Africa. By the year 2011, five countries (Ethiopia, Nigeria, China, India, and Russia) with 40 percent of the world's population will add 50 to 75 million infected people to the worldwide pool of HIV disease. An estimated one million people are currently living with HIV in the United States, with approximately 40,000 new infections occurring each year. FDA-approved antiviral drugs are currently in use, but increasing resistance to existing countermeasures necessitates the development of new antiviral therapeutics and treatment regimens/drug combinations to combat this lifelong infection.

Paramyxoviridae

Respiratory syncytial virus (RSV) is a nonsegmented, negative-strand RNA virus in the Paramyxoviridae family. The RNA codes for ten viral proteins-three are associated with the nucleocapsid (NS1, NS2, N), three with the envelope (SH, G, & F), two non-glycoslyated matrix proteins (M and M2), a phosphoprotein (P), and a major polymerase subunit (L). RSV ollness begins most frequently with fever, runny nose, cough, and sometimes wheezing. During their first RSV infection, between 25% and 40% of infants and young children have signs or symptoms of bronchiolitis or pneumonia, and 0.5% to 2% require hospitalization. Most children recover from illness in 8 to 15 days. The majority of children hospitalized for RSV infection are under 6 months of age. RSV also causes repeated infections throughout life, usually associated with moderate-to-severe cold-like symptoms; however, severe lower respiratory tract disease may occur at any age, especially among the elderly or among those with compromised cardiac, pulmonary, or immune systems. RSV is spread from respiratory secretions through close contact with infected persons or contact with contaminated surfaces or objects. Infection can occur when infectious material contacts mucous membranes of the eyes, mouth, or nose, and possibly through the inhalation of droplets generated by a sneeze or cough. In temperate climates, RSV infections usually occur during annual community outbreaks, often lasting 4 to 6 months, during the late fall, winter, or early spring months. The timing and severity of outbreaks in a community vary from year to year. RSV spreads efficiently among children during the annual outbreaks, and most children will have serologic evidence of RSV infection by 2 years of age.

RSV infects most children by age 2 and is the leading cause of bronchiolitis and pneumonia in infants. It can also be a significant cause of disease in immunocompromised adults and the elderly. Estimates vary on the actual number of cases, the most important of which are those involving hospitalization. One report (CDC) estimates that up to 126,300 children are hospitalized in the US each year. Another report describes a more global view, which estimates that "a total of 18 million people annually become infected by RSV in the US, Japan, France, Germany, Italy, Spain, UK, including three million adults with underlying disease and almost 400,000 premature infants. Approximately 900,000 of the individuals in these risk groups are hospitalized for this infection each year.

Picornaviridae

Viruses in the family Picornaviridae replicate a positive sense, single-stranded genome and are transmitted as non-enveloped, infectious virions. Picornaviruses include the causative agents of such human diseases as the common cold, Polio, Hand-Foot-and-Mouth Disease, and Hepatitis A. These viruses are distributed across the globe, and a long-term international eradication effort is currently underway to control and eliminate poliovirus infection in humans. The significant respiratory and enteric disease burden caused by these pathogens worldwide has led to numerous campaigns to identify antiviral therapeutics and vaccines to combat picornavirus-associated diseases. Preparedness for the public health challenges posed by picornaviruses requires the development of new antibacterial therapeutics.

Chlamydiaceae

Chlamydiae are obligate intracellular bacteria that cause serious diseases in humans and animals of veterinary significance. Sexually transmitted infections caused by *C. trachomatis* affect approximately 92 million men and women worldwide, leading to a variety of pathologies including urethritis, cervicitis, salpingitis, pelvic inflammatory disease, ectopic pregnancy and infertility. The pathogen also causes blinding trachoma, which is the leading cause of preventable blindness, primarily in underdeveloped countries. *Chlamydia pneumoniae* is a significant cause of respiratory infections, and there is evidence that these infections predispose individuals to atherosclerosis and perhaps other chronic conditions. Veterinary infections by a set of different chlamydiae lead to epidemic in a diverse collection of species, and some of these can manifest as zoonoses in humans having contact with infected animals. *Chlamydia psittaci*, one such zoonotic agent, is considered a potential biothreat agent. Preparedness for both biodefense and for the public health challenges posed by *C. burnetii* requires the development of new antibacterial therapeutics.

Coxiellaceae

*Coxiella burnetii* is a zoonotic pathogen of ruminants that can be acquired by humans through contact with infected aerosols. *C. burnetti* is the etiologic agent of Q fever. Following an initial flu-like illness, which occurs within 2-3 weeks of exposure to the bacteria, a subset of Q fever patients develop pneumonia or hepatitis. 1%-2% of people with acute Q fever die of the disease. Acute infections can also give rise to chronic disease, which may lead to endocarditis and death in infected individuals. *C. burnetii* is a highly infectious agent that is rather resistant to heat and drying. It can become airborne and inhaled by humans. A single *C. burnetii* organism may cause disease in a susceptible person. This agent could be developed for use in biological warfare and is considered a potential terrorist threat. Current treatment options for acute disease include doxycycline. For chronic disease treatment, protocols combine doxycycline and quinolones. Preparedness for both biodefense and for the public health challenges posed by *C. burnetii* requires the development of new antibacterial therapeutics.

SUMMARY OF THE INVENTION

The present invention provides a pharmaceutical composition comprising a pharmaceutically acceptable carrier and a compound having the following general Formula I or a pharmaceutically acceptable salt thereof:

Formula I

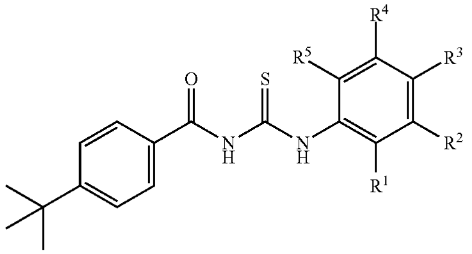

wherein $R^1$ is selected from the group consisting of: H, chloro, methyl, methoxy, ethoxy, nitro and fluoro;

$R^2$ is selected from the group consisting of: H, chloro, methyl, methoxy, trifluoromethyl, propanoylamino and 2-methylpropanoylamino;

$R^3$ is selected from the group consisting of: H, methyl, amino, methylamino, dimethylamino, phenylamino and 3-pyridylamino;

$R^4$ is selected from the group consisting of: H, chloro, methyl, methoxy, trifluoromethyl and trifluoromethoxy; and $R^5$ is selected from the group consisting of H and methyl.

The present invention also provides a method for the treatment or prophylaxis of a viral or bacterial infection or disease associated therewith, comprising administering in a therapeutically effective amount to a mammal in need thereof, a compound of Formula I below or a pharmaceutically acceptable salt thereof:

Formula I

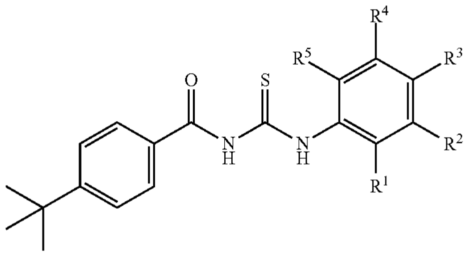

wherein $R^1$ is selected from the group consisting of: H, chloro, methyl, methoxy, ethoxy, nitro and fluoro;

$R^2$ is selected from the group consisting of: H, chloro, methyl, methoxy, trifluoromethyl, propanoylamino and 2-methylpropanoylamino;

$R^3$ is selected from the group consisting of: H, methyl, amino, methylamino, dimethylamino, phenylamino and 3-pyridylamino;

$R^4$ is selected from the group consisting of: H, chloro, methyl, methoxy, trifluoromethyl and trifluoromethoxy; and $R^5$ is selected from the group consisting of H and methyl.

The present invention further provides a compound selected from the group consisting of: N-[(4-amino-3-methoxy-phenyl)carbamothioyl]-4-tert-butyl-benzamide; N-[(4-amino-2-chloro-phenyl)carbamothioyl]-4-tert-butyl-benzamide hydrochloride; 4-tert-butyl-N-[[2-chloro-4-(methylamino)phenyl]-carbamothioyl]benzamide hydrochloride; 4-tert-butyl-N-[(2-chloro-5-methyl-phenyl)-carbamothioyl]benzamide; 4-tert-butyl-N-[(2-chloro-6-methyl-phenyl)-carbamothioyl]benzamide; 4-tert-butyl-N-[[2-chloro-3-(trifluoromethyl)phenyl]-carbamothioyl] benzamide; N-[(4-amino-3-methoxy-phenyl) carbamothioyl]-4-tert-butyl-benzamide hydrochloride; 4-tert-butyl-N-[(2-chloro-3-methyl-phenyl)-carbamothioyl] benzamide; 4-tert-butyl-N-[[4-(methylamino)phenyl]-carbamothioyl]benzamide hydrochloride; 4-tert-butyl-N-[[2-chloro-4-(dimethylamino)phenyl]-carbamothioyl] benzamide hydrochloride; 4-tert-butyl-N-[[2-chloro-5-(trifluoromethoxy)phenyl]-carbamothioyl]benzamide; and 4-tert-butyl-N-[[4-(3-pyridylamino)phenyl]-carbamothioyl] benzamide hydrochloride.

The present invention also provides a pharmaceutical composition comprising a pharmaceutically acceptable carrier and a compound having the following general Formula II or a pharmaceutically acceptable salt thereof:

Formula II

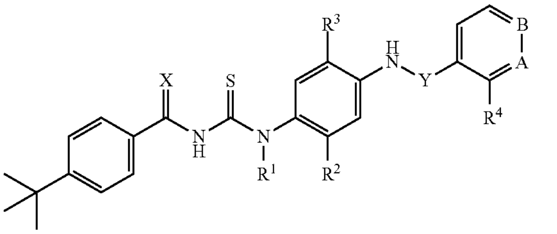

wherein X is selected from the group consisting of oxygen and NH;

Y is selected from the group consisting of: —$CH_2$—, —C(═O)—, —C(═S)—and —C(═NH)—;

A is selected from the group consisting of: N and $CR^5$;

B is selected from the group consisting of: N and $CR^6$;

$R^1$ is selected from the group consisting of: hydrogen and ethyl;

$R^2$ is selected from the group consisting of: hydrogen and chloro;

$R^3$ is selected from the group consisting of: hydrogen, methoxy, amino and hydroxyl;

$R^4$ is selected from the group consisting of: hydrogen, chloro and amino;

$R^5$ is selected from the group consisting of hydrogen and aminomethyl; and $R^6$ is selected from the group consisting of hydrogen, amino and aminomethyl.

The present invention further provides a method for the treatment or prophylaxis of a viral or bacterial infection or disease associated therewith, comprising administering in a therapeutically effective amount to a mammal in need thereof, a compound of Formula II below or a pharmaceutically acceptable salt thereof:

Formula II

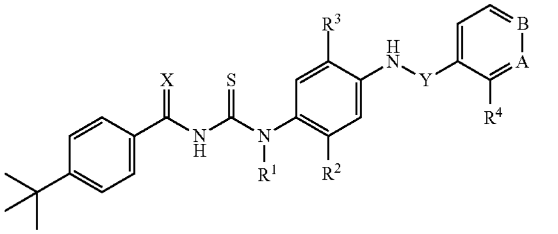

wherein X is selected from the group consisting of oxygen and NH;

Y is selected from the group consisting of: —$CH_2$—, —C(═O)—, —C(═S)—and —C(═NH)—;

A is selected from the group consisting of: N and $CR^5$;

B is selected from the group consisting of: N and $CR^6$;

$R^1$ is selected from the group consisting of: hydrogen and ethyl;

$R^2$ is selected from the group consisting of: hydrogen and chloro;

$R^3$ is selected from the group consisting of: hydrogen, methoxy, amino and hydroxyl;

$R^4$ is selected from the group consisting of: hydrogen, chloro and amino;

$R^5$ is selected from the group consisting of hydrogen and aminomethyl; and $R^6$ is selected from the group consisting of hydrogen, amino and aminomethyl.

The present invention also provides a compound selected from the group consisting of: N-[4-[(4-tert-butylbenzoyl)-carbamothioylamino]-2-hydroxy-phenyl]-2-chloro-benzamide; 4-tert-butyl-N-[[4-[(2-chlorophenyl)-methylamino]-3-methoxy-phenyl]-carbamothioyl]-benzamide; N-[2-amino-4-[(4-tert-butylbenzoyl)-carbamothioylamino]-phenyl]-2-chloro-benzamide hydrochloride; N-[(4-benzamido-2-chloro-phenyl)carbamothioyl]-4-tert-butyl-benzamide; 4-tert-butyl-N-[[4-[(2-chlorobenzene-carbothioyl)amino]-3-methoxy-phenyl]-carbamothioyl] benzamide; 4-(aminomethyl)-N-[4-[(4-tert-butylbenzoyl)-carbamothioylamino]-2-methoxy-phenyl]benzamide hydrochloride; N-[4-[(4-tert-butylbenzene-carboximidoyl)-carbamothioylamino]-2-methoxy-phenyl]-2-chloro-benzamide; 4-tert-butyl-N-[[4-[(2-chlorobenzene-carboximidoyl)amino]-3-methoxy-phenyl]-carbamothioyl] benzamide; 3-(aminomethyl)-N-[4-[(4-tert-butylbenzoyl)-carbamothioylamino]-2-methoxy-phenyl]benzamide hydrochloride; 2-amino-N-[4-[(4-tert-butylbenzoyl)-carbamothioylamino]-2-methoxy-phenyl]benzamide; N-[4-[(4-tert-butylbenzoyl)-carbamothioylamino]-2-methoxy-phenyl]pyridine-3-carboxamide; N-[4-[(4-tert-butylbenzoyl)-carbamothioylamino]-2-methoxy-phenyl]pyridine-4-carboxamide; N-[[4-[(4-aminobenzoyl)amino]-3-methoxy-phenyl]-carbamothioyl]-4-tert-butyl-benzamide hydrochloride; and N-[4-[(4-tert-butylbenzoyl)-carbamothioyl-ethyl-amino]-2-methoxy-phenyl]-2-chloro-benzamide.

The present invention further provides a pharmaceutical composition comprising a pharmaceutically acceptable carrier and a compound having the following general Formula III or a pharmaceutically acceptable salt thereof:

Formula III

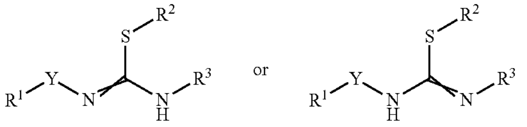

or wherein Y is absent or is selected from the group consisting of: —$CH_2$—, —C(═O)—, —C(═S)—and —C(═NH)—;

$R^1$ is selected from the group consisting of aryl, cycloalkane and alkyl;

$R^2$ is alkyl; and $R^3$ is selected from the group consisting of: aryl, cycloalkane and alkyl.

The present invention also provides a method for the treatment or prophylaxis of a viral or bacterial infection or disease associated therewith, comprising administering in a therapeutically effective amount to a mammal in need thereof, a compound of Formula III below or a pharmaceutically acceptable salt thereof:

Formula III

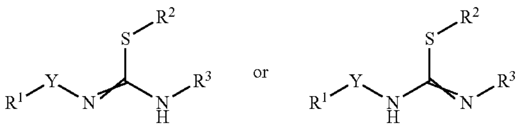

or wherein Y is absent or is selected from the group consisting of: —$CH_2$—, —C(═O)—, —C(═S)—and —C(═NH)—;

$R^1$ is selected from the group consisting of aryl, cycloalkane and alkyl;

$R^2$ is alkyl; and $R^3$ is selected from the group consisting of: aryl, cycloalkane and alkyl.

The present invention further provides a compound having the following general Formula III or a pharmaceutically acceptable salt thereof:

Formula III

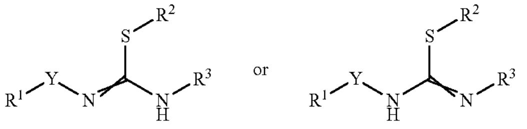

or wherein Y is absent or is selected from the group consisting of: —$CH_2$—, —C(═O)—, —C(═S)—and —C(═NH)—;

$R^1$ is selected from the group consisting of aryl, cycloalkane and alkyl;

$R^2$ is alkyl; and $R^3$ is selected from the group consisting of: aryl, cycloalkane and alkyl.

The present invention also provides a pharmaceutical composition comprising a pharmaceutically acceptable carrier and a compound selected from the group consisting of: 4-tert-butyl-N-[[4-[[5-(dimethylamino)-1-naphthyl]sulfonylamino]-3-methoxy-phenyl]-carbamothioyl]benzamide; N-[(3-aminophenyl)-carbamothioyl]-4-tert-butyl-benzamide; N-[(4-acetamido-3-methoxy-phenyl)-carbamothioyl]-4-tert-butyl-benzamide; 4-tert-butyl-N-[[3-methoxy-4-[5-(2-oxo-1,3,3a,4,6,6a-hexahydrothieno[3,4-d]imidazol-4-yl)-pentanoylamino]phenyl]-carbamothioyl]benzamide; 2-chloro-N-[4-(cyclohexanecarbonyl-carbamothioylamino)-2-methoxy-phenyl]benzamide; 2-chloro-N-[4-(ethylcarbamo-thioylamino)-2-methoxy-phenyl]benzamide; methyl 3-[4-[(4-tert-butylbenzoyl)carbamo-thioylamino]-2-methoxy-anilino]-3-oxo-propanoate; 4-tert-butyl-N-[(3-methoxy-4-ureido-phenyl)carbamothioyl]-benzamide; 4-tert-butyl-N-[[4-(4-pyridylamino)phenyl]-carbamothioyl] benzamide hydrochloride; N-[[4-[(4-tert-butylbenzoyl) amino]phenyl]carbamothioyl]-4-methyl-benzamide; 4-tert-butyl-N-[(5-tert-butyl-2-hydroxy-phenyl)-carbamothioyl] benzamide; 4-tert-butyl-N-(cyclohexyl-carbamothioyl) benzamide; 4-tert-butyl-N-[(4-methoxyphenyl)-carbamothioyl]benzamide; 4-tert-butyl-N-[(4-nitrophenyl)-carbamothioyl]benzamide; 4-tert-butyl-N-[(3-cyano-4,5-dimethyl-2-thienyl)-carbamothioyl]benzamide; 4-tert-butyl-N-(ethylcarbamothioyl)-benzamide; and N-[3-[(4-tert-butylbenzoyl)-carbamothioylamino]phenyl]-2-chloro-benzamide.

The present invention further provides a method for the treatment or prophylaxis of a viral or bacterial infection or disease associated therewith, comprising administering in a therapeutically effective amount to a mammal in need thereof, a compound selected from the group consisting of: 4-tert-butyl-N-[[4-[[5-(dimethylamino)-1-naphthyl]sulfonylamino]-3-methoxy-phenyl]-carbamothioyl]benzamide; N-[(3-aminophenyl)-carbamothioyl]-4-tert-butyl-benzamide; N-[(4-acetamido-3-methoxy-phenyl)-carbamothioyl]-4-tert-butyl-benzamide; 4-tert-butyl-N-[[3-methoxy-4-[5-(2-oxo-1,3,3a,4,6,6a-hexahydrothieno[3,4-d]imidazol-4-yl)-pentanoylamino]phenyl]-carbamothioyl]benzamide; 2-chloro-N-[4-(cyclohexanecarbonyl-carbamothioylamino)-2-methoxy-phenyl]benzamide; 2-chloro-N-[4-(ethylcarbamo-thioylamino)-2-methoxy-phenyl]benzamide; methyl 3-[4-[(4-tert-butylbenzoyl)carbamo-thioylamino]-2-methoxy-anilino]-3-oxo-propanoate; 4-tert-butyl-N-[(3-methoxy-4-ureido-phenyl)carbamothioyl]-benzamide; 4-tert-butyl-N-[[4-(4-pyridylamino)phenyl]-carbamothioyl] benzamide hydrochloride; N-[[4-[(4-tert-butylbenzoyl) amino]phenyl]carbamothioyl]-4-methyl-benzamide; 4-tert-butyl-N-[(5-tert-butyl-2-hydroxy-phenyl)-carbamothioyl] benzamide; 4-tert-butyl-N-(cyclohexyl-carbamothioyl) benzamide; 4-tert-butyl-N-[(4-methoxyphenyl)-carbamothioyl]benzamide; 4-tert-butyl-N-[(4-nitrophenyl)-carbamothioyl]benzamide; 4-tert-butyl-N-[(3-cyano-4,5-dimethyl-2-thienyl)-carbamothioyl]benzamide; 4-tert-butyl-N-(ethylcarbamothioyl)-benzamide; and N-[3-[(4-tert-butylbenzoyl)-carbamothioylamino]phenyl]-2-chloro-benzamide.

The present invention also provides a compound selected from the group consisting of: 4-tert-butyl-N-[[4-[[5-(dimethylamino)-1-naphthyl]sulfonylamino]-3-methoxy-phenyl]-carbamothioyl]benzamide; N-[(3-aminophenyl)-carbamothioyl]-4-tert-butyl-benzamide; N-[(4-acetamido-3-methoxy-phenyl)-carbamothioyl]-4-tert-butyl-benzamide; 4-tert-butyl-N-[[3-methoxy-4-[5-(2-oxo-1,3,3a,4,6,6a-hexahydrothieno[3,4-d]imidazol-4-yl)-pentanoylamino]phenyl]-carbamothioyl]benzamide; 2-chloro-N-[4-(cyclohexanecarbonyl-carbamothioylamino)-2-methoxy-phenyl]benzamide; 2-chloro-N-[4-(ethylcarbamo-thioylamino)-2-methoxy-phenyl]benzamide; methyl 3-[4-[(4-tert-butylbenzoyl)carbamo-thioylamino]-2-methoxy-anilino]-3-oxo-propanoate; 4-tert-butyl-N-[(3-methoxy-4-ureido-phenyl)carbamothioyl]-benzamide; and 4-tert-butyl-N-[[4-(4-pyridylamino) phenyl]-carbamothioyl]benzamide hydrochloride.

Other objects and advantages of the present invention will become apparent from the following description and appended claims.

DETAILED DESCRIPTION OF THE INVENTION

The compounds of the invention include compounds which are of the following general Formula I or a pharmaceutically acceptable salt thereof:

Formula I

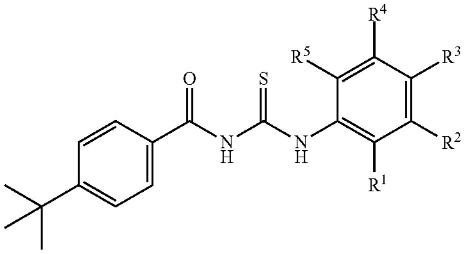

wherein $R^1$ is selected from the group consisting of: H, chloro, methyl, methoxy, ethoxy, nitro and fluoro;

$R^2$ is selected from the group consisting of: H, chloro, methyl, methoxy, trifluoromethyl, propanoylamino and 2-methylpropanoylamino;

$R^3$ is selected from the group consisting of: H, methyl, amino, methylamino, dimethylamino, phenylamino and 3-pyridylamino;

$R^4$ is selected from the group consisting of: H, chloro, methyl, methoxy, trifluoromethyl and trifluoromethoxy; and $R^5$ is selected from the group consisting of H and methyl.

Preferably, $R^1$ is hydrogen or chloro; $R^2$ is hydrogen or trifluoromethyl; $R^3$ is amino or methylamino; $R^4$ is hydrogen or methoxy; and $R^5$ is hydrogen.

Preferably, the compound of Formula I of the present is selected from the group consisting of: N-[(4-amino-3-methoxy-phenyl)carbamothioyl]-4-tert-butyl-benzamide; N-[(4-amino-2-chloro-phenyl)carbamothioyl]-4-tert-butyl-benzamide hydrochloride; 4-tert-butyl-N-[[2-chloro-4-(methylamino)phenyl]-carbamothioyl]benzamide hydrochloride; 4-tert-butyl-N-[(2-chloro-5-methyl-phenyl)-carbamothioyl]benzamide; 4-tert-butyl-N-[(2-chloro-6-methyl-phenyl)-carbamothioyl]benzamide; 4-tert-butyl-N-[[2-chloro-3-(trifluoromethyl)phenyl]-carbamothioyl] benzamide; N-[(4-amino-3-methoxy-phenyl) carbamothioyl]-4-tert-butyl-benzamide hydrochloride; 4-tert-butyl-N-[(2-chloro-3-methyl-phenyl)-carbamothioyl] benzamide; 4-tert-butyl-N-[[4-(methylamino)phenyl]-carbamothioyl]benzamide hydrochloride; 4-tert-butyl-N-[[2-chloro-4-(dimethylamino)phenyl]-carbamothioyl] benzamide hydrochloride; 4-tert-butyl-N-[[2-chloro-5-(trifluoromethoxy)phenyl]-carbamothioyl]benzamide; 4-tert-butyl-N-[[4-(3-pyridylamino)phenyl]-carbamothioyl] benzamide hydrochloride; 4-tert-butyl-N-[(2-chlorophenyl) carbamothioyl]-benzamide; 4-tert-butyl-N-(o-tolylcarbamothioyl)-benzamide; 4-tert-butyl-N-[[2-chloro-5-(trifluoromethyl)phenyl]-carbamothioyl]benzamide; N-[(4-anilinophenyl)-carbamothioyl]-4-tert-butyl-benzamide; 4-tert-butyl-N-[(3-chloro-2-methyl-phenyl)-carbamothioyl] benzamide; 4-tert-butyl-N-[(2,4-dimethylphenyl)-carbamothioyl]benzamide; 4-tert-butyl-N-[(4-dimethylaminophenyl)-carbamothioyl]benzamide; 4-tert-butyl-N-[(2,5-dichlorophenyl)-carbamothioyl]benzamide; 4-tert-butyl-N-[(2-methoxyphenyl)-carbamothioyl]benzamide; 4-tert-butyl-N-[(3-chlorophenyl)-carbamothioyl]benzamide; 4-tert-butyl-N-(phenylcarbamothioyl)-benzamide; 4-tert-butyl-N-[(2,3-dimethylphenyl)-carbamothioyl]benzamide; 4-tert-butyl-N-[(3,4-dimethylphenyl)-carbamothioyl]benzamide; 4-tert-butyl-N-[(2-ethoxyphenyl)-carbamothioyl] benzamide; 4-tert-butyl-N-[[3-(2-methylpropanoylamino)-phenyl]carbamothioyl]-benzamide; 4-tert-butyl-N-[(2-nitrophenyl)carbamothioyl]-benzamide; 4-tert-butyl-N-(p-tolylcarbamothioyl)-benzamide; N-[(4-aminophenyl)-carbamothioyl]-4-tert-butyl-benzamide; 4-tert-butyl-N-[(2-fluorophenyl)carbamothioyl]-benzamide; 4-tert-butyl-N-[[3-(propanoylamino)phenyl]-carbamothioyl]benzamide; 4-tert-butyl-N-(m-tolylcarbamothioyl)-benzamide; 4-tert-butyl-N-[(3,5-dimethylphenyl)-carbamothioyl]benzamide; 4-tert-butyl-N-[(3-methoxyphenyl)-carbamothioyl]benzamide; 4-tert-butyl-N-[(2,5-dimethylphenyl)-carbamothioyl]benzamide; 4-tert-butyl-N-[(4-dimethylaminophenyl)-carbamothioyl]benzamide hydrochloride; and 4-tert-butyl-N-[(2,6-dimethylphenyl)-carbamothioyl]benzamide.

More preferably, the compound of Formula I 4-tert-butyl-N-[(2-chloro-5-methyl-phenyl) -carbamothioyl]benzamide.

TABLE 1

List of certain novel compounds of Formula I of the present invention.

| Compound | Chemical Structure | Molecular Formula | Analytical Data | Chemical Name |
|---|---|---|---|---|
| 1 | 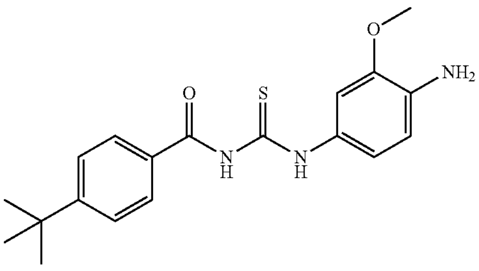 [SMILES: COc1cc(NC(=S)NC(=O)c2ccc(C(C)(C)C)cc2)ccc1N] | C19H23N3O2S | 1H NMR in DMSO-d6: δ 12.53 (s, 1H), 11.26 (s, 1H), 7.94 (d, 2H), 7.56 (d, 2H), 7.25 (d, 1H), 6.96 (dd, 1H), 6.63 (d, 1H), 4.83 (s, 2H), 3.77 (s, 3H), 1.32 (s, 9H); Mass Spec: 358.1 $(M + H)^+$ | N-[(4-amino-3-methoxy-phenyl)carbamothioyl]-4-tert-butyl-benzamide |

TABLE 1-continued

List of certain novel compounds of Formula I of the present invention.

| Compound | Chemical Structure | Molecular Formula | Analytical Data | Chemical Name |
|---|---|---|---|---|
| 4 | 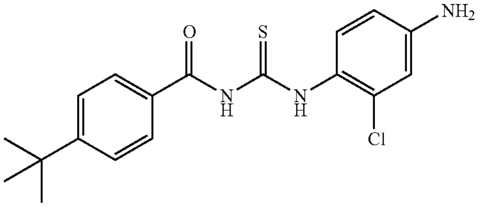 [SMILES: CC(C)(C)c1ccc(C(=O)NC(=S)Nc2ccc(N)cc2Cl)cc1] | C18H20ClN3OS HCl | 1H NMR in DMSO-d6: δ 12.42 (s, 1H), 11.52 (s, 1H), 7.95 (d, 2H), 7.55-7.63 (m, 3H), 6.84 (br, 1H), 6.69 (br, 1H), 1.32 (s, 9H); Mass Spec: 361.9 $(M + H)^+$; 384.0 $(M + Na)^+$ | N-[(4-amino-2-chloro-phenyl)carbamothioyl]-4-tert-butyl-benzamide hydrochloride |
| 5 | 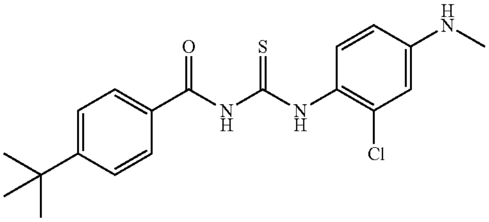 [SMILES: CNc1ccc(NC(=S)NC(=O)c2ccc(C(C)(C)C)cc2)c(Cl)c1] | C19H22ClN3OS HCl | 1H NMR in DMSO-d6: δ 12.41 (s, 1H), 11.50 (s, 1H), 7.95 (d, 2H), 7.60 (d, 1H), 7.56 (d, 2H), 6.66 (d, 1H), 6.56 (dd, 1H), 2.70 (s, 3H), 1.32 (s, 9H); Mass Spec: 375.9 $(M + H)^+$; 397.9 $(M + Na)^+$ | 4-tert-butyl-N-[[2-chloro-4-(methylamino)phenyl]-carbamothioyl]benzamide hydrochloride |
| 11 | 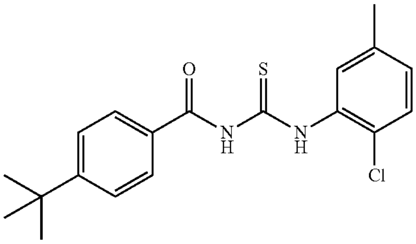 [SMILES: Cc1ccc(Cl)c(NC(=S)NC(=O)c2ccc(C(C)(C)C)cc2)c1] | C19H21ClN2OS | 1H NMR in DMSO-d6: δ 12.69 (s, 1H), 11.65 (s, 1H), 7.97 (d, 2H), 7.87 (s, 1H), 7.57 (d, 2H), 7.46 (d, 1H), 7.15 (dd, 1H), 2.33 (s, 3H), 1.33 (s, 9H); Mass Spec: 361.0 $(M + H)^+$; 382.8 $(M + Na)^+$ | 4-tert-butyl-N-[(2-chloro-5-methyl-phenyl)-carbamothioyl]benzamide |
| 13 | 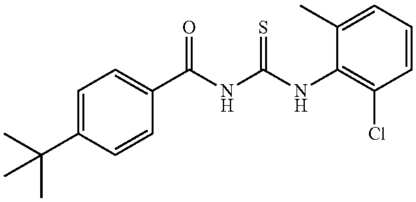 [SMILES: Cc1cccc(Cl)c1NC(=S)NC(=O)c1ccc(C(C)(C)C)cc1] | C19H21ClN2OS | 1H NMR in DMSO-d6: δ 12.05 (s, 1H), 11.63 (s, 1H), 7.99 (d, 2H), 7.57 (d, 2H), 7.37-7.42 (m, 1H), 7.25-7.31 (m, 2H), 2.27 (s, 3H), 1.33 (s, 9H); Mass Spec: 360.9 $(M + H)^+$; 382.9 $(M + Na)^+$ | 4-tert-butyl-N-[(2-chloro-6-methyl-phenyl)-carbamothioyl]benzamide |
| 15 | 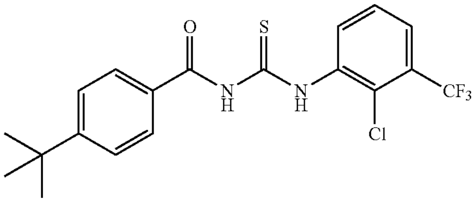 [SMILES: CC(C)(C)c1ccc(C(=O)NC(=S)Nc2cccc(C(F)(F)F)c2Cl)cc1] | C19H18ClF3N2OS | 1H NMR in DMSO-d6: δ 12.67 (s, 1H), 11.80 (s, 1H), 8.17 (d, 1H), 7.98 (d, 2H), 7.83 (d, 1H), 7.63 (t, 1H), 7.58 (d, 2H), 1.33 (s, 9H); Mass Spec: 414.7 $(M + H)^+$ | 4-tert-butyl-N-[[2-chloro-3-(trifluoromethyl)phenyl]-carbamothioyl]benzamide |
| 18 | 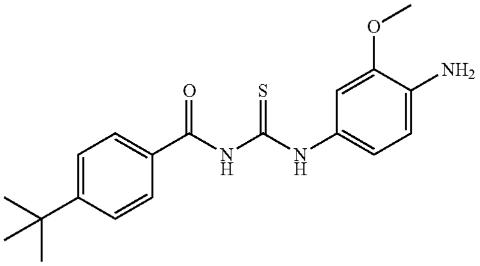 [SMILES: COc1cc(NC(=S)NC(=O)c2ccc(C(C)(C)C)cc2)ccc1N] | C19H23N3O2S HCl | 1H NMR in DMSO-d6: δ 12.70 (s, 1H), 11.50 (s, 1H), 7.95 (d, 2H), 7.62 (s, 1H), 7.57 (d, 2H), 7.29-7.38 (m, 2H), 3.89 (s, 3H), 1.32 (s, 9H); Mass Spec: 358.0 $(M + H)^+$; 380.0 $(M + Na)^+$ | N-[(4-amino-3-methoxy-phenyl)carbamothioyl]-4-tert-butyl-benzamide hydrochloride |

TABLE 1-continued

List of certain novel compounds of Formula I of the present invention.

| Compound | Chemical Structure | Molecular Formula | Analytical Data | Chemical Name |
|---|---|---|---|---|
| 19 | 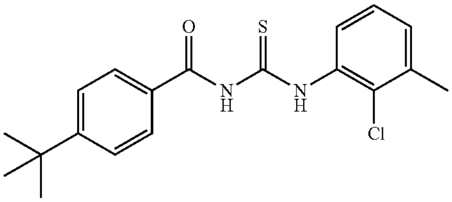 [SMILES: Cc1cccc(NC(=S)NC(=O)c2ccc(C(C)(C)C)cc2)c1Cl] | C19H21ClN2OS | 1H NMR in DMSO-d6: δ 12.73 (s, 1H), 11.65 (s, 1H), 7.97 (d, 2H), 7.87 (t, 1H), 7.57 (d, 2H), 7.31 (d, 2H), 2.40 (s, 3H), 1.33 (s, 9H); Mass Spec: 361.0 $(M + H)^+$; 383.0 $(M + Na)^+$ | 4-tert-butyl-N-[(2-chloro-3-methyl-phenyl)-carbamothioyl]benzamide |
| 21 | 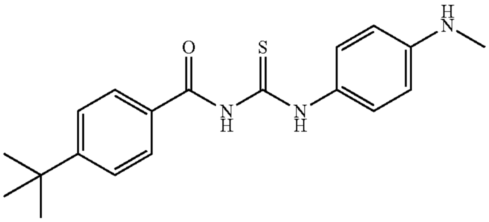 [SMILES: CNc1ccc(NC(=S)NC(=O)c2ccc(C(C)(C)C)cc2)cc1] | C19H23N3OS HCl | 1H NMR in DMSO-d6: δ 12.52 (s, 1H), 11.34 (s, 1H), 7.94 (d, 2H), 7.56 (d, 2H), 7.51 (d, 2H), 6.85 (br, 2H), 2.77 (s, 3H), 1.32 (s, 9H); Mass Spec: 342.0 $(M + H)^+$; 364.0 $(M + Na)^+$ | 4-tert-butyl-N-[[4-(methylamino)phenyl]-carbamothioyl]benzamide hydrochloride |
| 22 | 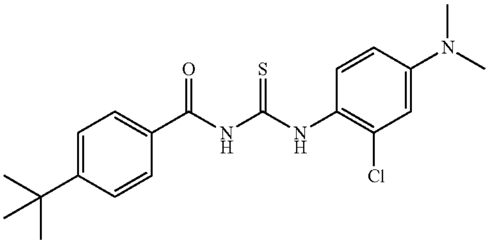 [SMILES: CN(C)c1ccc(NC(=S)NC(=O)c2ccc(C(C)(C)C)cc2)c(Cl)c1] | C20H24ClN3OS HCl | 1H NMR in DMSO-d6: δ 12.48 (s, 1H), 11.52 (s, 1H), 7.96 (d, 2H), 7.72 (d, 1H), 7.56 (d, 2H), 6.80 (d, 1H), 6.73 (dd, 1H), 2.94 (s, 6H), 1.32 (s, 9H); Mass Spec: 390.0 $(M + H)^+$; 411.9 $(M + Na)^+$ | 4-tert-butyl-N-[[2-chloro-4-(dimethylamino)phenyl]-carbamothioyl]benzamide hydrochloride |
| 29 | 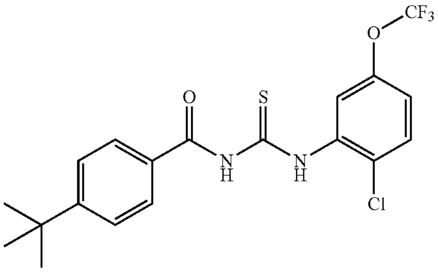 [SMILES: CC(C)(C)c1ccc(C(=O)NC(=S)Nc2cc(OC(F)(F)F)ccc2Cl)cc1] | C19H18ClF3N2O2S | 1H NMR in DMSO-d6: δ 12.95 (br, 1H), 11.81 (br, 1H), 8.34 (d, 1H), 7.97 (d, 2H), 7.75 (d, 1H), 7.58 (d, 2H), 7.37 (dd, 1H), 1.33 (s, 9H) | 4-tert-butyl-N-[[2-chloro-5-(trifluoromethoxy)phenyl]-carbamothioyl]benzamide |
| 36 | 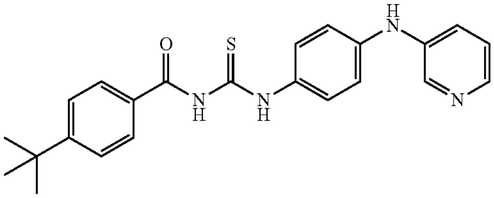 [SMILES: CC(C)(C)c1ccc(C(=O)NC(=S)Nc2ccc(Nc3cccnc3)cc2)cc1] | C23H24N4OS HCl | 1H NMR in DMSO-d6: δ 12.64 (s, 1H), 11.43 (s, 1H), 9.81 (br, 1H), 8.46 (d, 1H), 8.22 (d, 1H), 8.09 (dd, 1H), 7.96 (d, 2H), 7.78 (dd, 1H), 7.70 (d, 2H), 7.57 (d, 2H), 7.32 (d, 2H), 1.32 (s, 9H); Mass Spec: 405.1 $(M + H)^+$; 427.1 $(M + Na)^+$ | 4-tert-butyl-N-[[4-(3-pyridylamino)phenyl]-carbamothioyl]benzamide hydrochloride |

TABLE 2

List of certain compounds of Formula I of the present invention.

| Compound | Chemical Structure | Molecular Formula | Chemical Name |
|---|---|---|---|
| 40 | 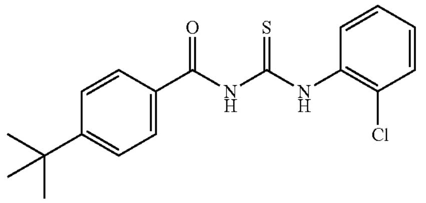 [SMILES: CC(C)(C)c1ccc(C(=O)NC(=S)Nc2ccccc2Cl)cc1] | C18H19ClN2OS | 4-tert-butyl-N-[(2-chlorophenyl)carbamothioyl]-benzamide |
| 42 | 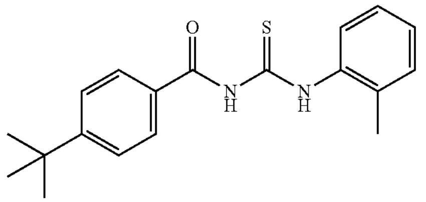 [SMILES: Cc1ccccc1NC(=S)NC(=O)c1ccc(C(C)(C)C)cc1] | C19H22N2OS | 4-tert-butyl-N-(o-tolylcarbamothioyl)-benzamide |
| 44 | 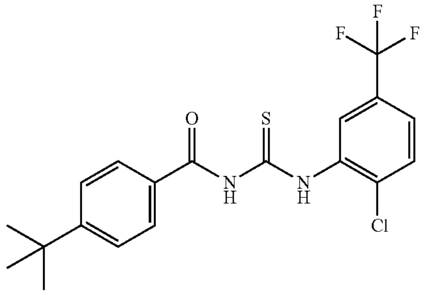 [SMILES: CC(C)(C)c1ccc(C(=O)NC(=S)Nc2cc(C(F)(F)F)ccc2Cl)cc1] | C19H18ClF3N2OS | 4-tert-butyl-N-[[2-chloro-5-(trifluoromethyl)phenyl]-carbamothioyl]benzamide |
| 45 | 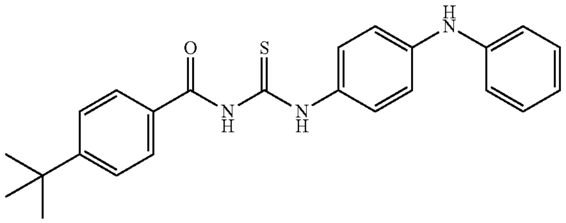 [SMILES: CC(C)(C)c1ccc(C(=O)NC(=S)Nc2ccc(Nc3ccccc3)cc2)cc1] | C24H25N3OS | N-[(4-anilinophenyl)-carbamothioyl]-4-tert-butyl-benzamide |
| 47 | 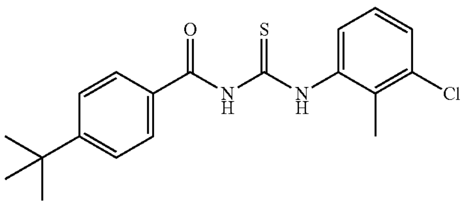 [SMILES: Cc1c(Cl)cccc1NC(=S)NC(=O)c1ccc(C(C)(C)C)cc1] | C19H21ClN2OS | 4-tert-butyl-N-[(3-chloro-2-methyl-phenyl)-carbamothioyl]benzamide |
| 48 | 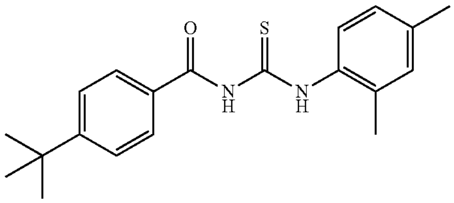 [SMILES: Cc1ccc(NC(=S)NC(=O)c2ccc(C(C)(C)C)cc2)c(C)c1] | C20H24N2OS | 4-tert-butyl-N-[(2,4-dimethylphenyl)-carbamothioyl]benzamide |

TABLE 2-continued

| List of certain compounds of Formula I of the present invention. | | | |
|---|---|---|---|
| Compound | Chemical Structure | Molecular Formula | Chemical Name |
| 49 | 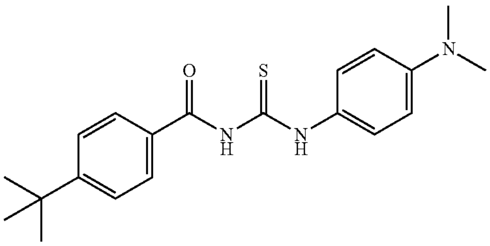 [SMILES: CN(C)c1ccc(NC(=S)NC(=O)c2ccc(C(C)(C)C)cc2)cc1] | C20H25N3OS | 4-tert-butyl-N-[(4-dimethylaminophenyl)-carbamothioyl]benzamide |
| 50 | 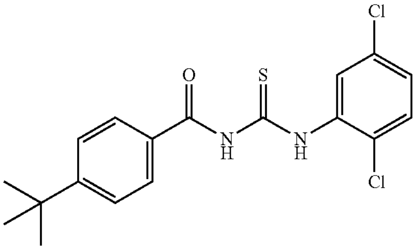 [SMILES: CC(C)(C)c1ccc(C(=O)NC(=S)Nc2cc(Cl)ccc2Cl)cc1] | C18H18Cl2N2OS | 4-tert-butyl-N-[(2,5-dichlorophenyl)-carbamothioyl]benzamide |
| 51 | 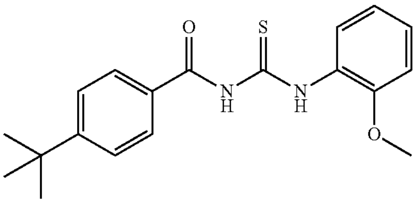 [SMILES: COc1ccccc1NC(=S)NC(=O)c1ccc(C(C)(C)C)cc1] | C19H22N2O2S | 4-tert-butyl-N-[(2-methoxyphenyl)-carbamothioyl]benzamide |
| 52 | 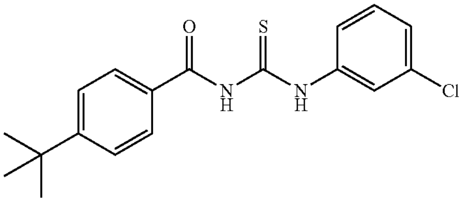 [SMILES: CC(C)(C)c1ccc(C(=O)NC(=S)Nc2cccc(Cl)c2)cc1] | C18H19ClN2OS | 4-tert-butyl-N-[(3-chlorophenyl)-carbamothioyl]benzamide |
| 53 | 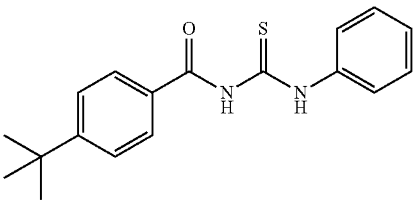 [SMILES: CC(C)(C)c1ccc(C(=O)NC(=S)Nc2ccccc2)cc1] | C18H20N2OS | 4-tert-butyl-N-(phenylcarbamothioyl)-benzamide |
| 54 | 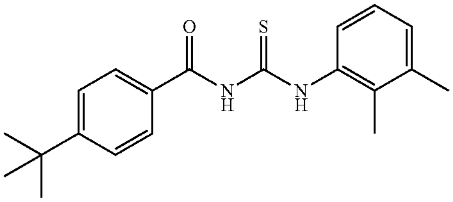 [SMILES: Cc1cccc(NC(=S)NC(=O)c2ccc(C(C)(C)C)cc2)c1C] | C20H24N2OS | 4-tert-butyl-N-[(2,3-dimethylphenyl)-carbamothioyl]benzamide |

TABLE 2-continued

List of certain compounds of Formula I of the present invention.

| Compound | Chemical Structure | Molecular Formula | Chemical Name |
|---|---|---|---|
| 55 | 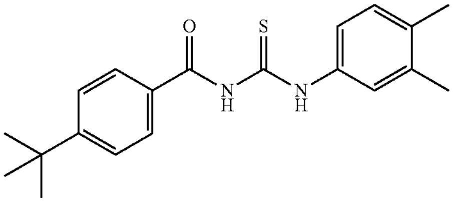 [SMILES: Cc1ccc(NC(=S)NC(=O)c2ccc(C(C)(C)C)cc2)cc1C] | C20H24N2OS | 4-tert-butyl-N-[(3,4-dimethylphenyl)-carbamothioyl]benzamide |
| 56 | 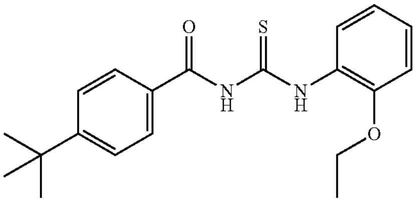 [SMILES: CCOc1ccccc1NC(=S)NC(=O)c1ccc(C(C)(C)C)cc1] | C20H24N2O2S | 4-tert-butyl-N-[(2-ethoxyphenyl)-carbamothioyl]benzamide |
| 57 | 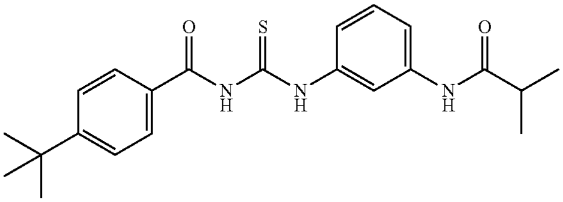 [SMILES: CC(C)C(=O)Nc1cccc(NC(=S)NC(=O)c2ccc(C(C)(C)C)cc2)c1] | C22H27N3O2S | 4-tert-butyl-N-[[3-(2-methylpropanoylamino)-phenyl]carbamothioyl]-benzamide |
| 58 | 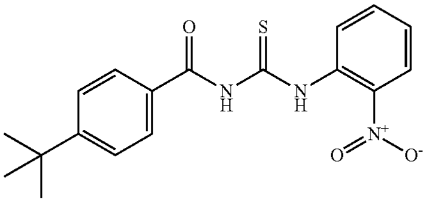 [SMILES: CC(C)(C)c1ccc(C(=O)NC(=S)Nc2ccccc2[N+](=O)[O-])cc1] | C18H19N3O3S | 4-tert-butyl-N-[(2-nitrophenyl)carbamothioyl]-benzamide |
| 59 | 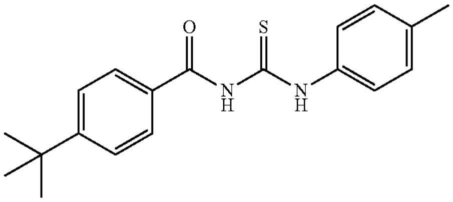 [SMILES: Cc1ccc(NC(=S)NC(=O)c2ccc(C(C)(C)C)cc2)cc1] | C19H22N2OS | 4-tert-butyl-N-(p-tolylcarbamothioyl)-benzamide |
| 60 | 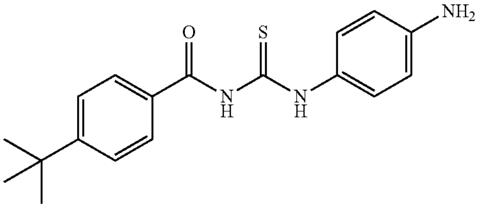 [SMILES: CC(C)(C)c1ccc(C(=O)NC(=S)Nc2ccc(N)cc2)cc1] | C18H21N3OS | N-[(4-aminophenyl)-carbamothioyl]-4-tert-butyl-benzamide |
| 61 | 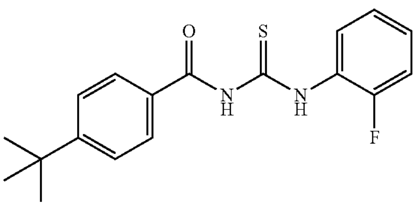 [SMILES: CC(C)(C)c1ccc(C(=O)NC(=S)Nc2ccccc2F)cc1] | C18H19FN2OS | 4-tert-butyl-N-[(2-fluorophenyl)carbamothioyl]-benzamide |

TABLE 2-continued

| List of certain compounds of Formula I of the present invention. | | | |
|---|---|---|---|
| Compound | Chemical Structure | Molecular Formula | Chemical Name |
| 62 | 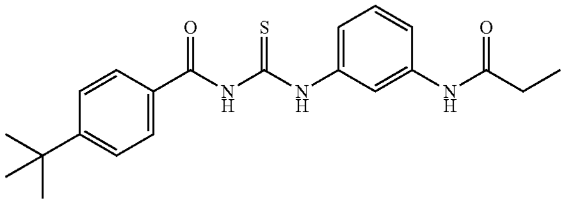 [SMILES: CCC(=O)Nc1cccc(NC(=S)NC(=O)c2ccc(C(C)(C)C)cc2)c1] | C21H25N3O2S | 4-tert-butyl-N-[[3-(propanoylamino)phenyl]-carbamothioyl]benzamide |
| 63 | 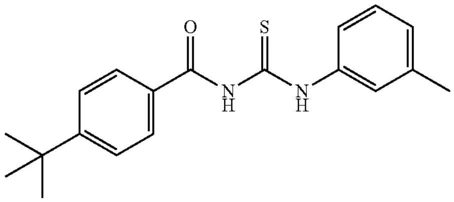 [SMILES: Cc1cccc(NC(=S)NC(=O)c2ccc(C(C)(C)C)cc2)c1] | C19H22N2OS | 4-tert-butyl-N-(m-tolylcarbamothioyl)-benzamide |
| 65 | 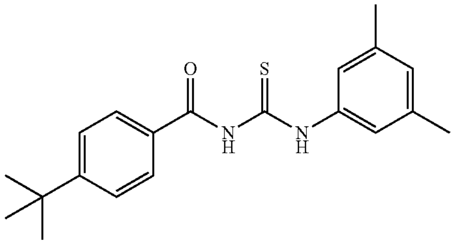 [SMILES: Cc1cc(C)cc(NC(=S)NC(=O)c2ccc(C(C)(C)C)cc2)c1] | C20H24N2OS | 4-tert-butyl-N-[(3,5-dimethylphenyl)-carbamothioyl]benzamide |
| 66 | 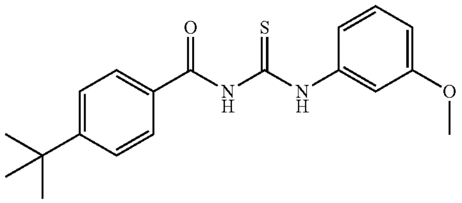 [SMILES: COc1cccc(NC(=S)NC(=O)c2ccc(C(C)(C)C)cc2)c1] | C19H22N2O2S | 4-tert-butyl-N-[(3-methoxyphenyl)-carbamothioyl]benzamide |
| 67 | 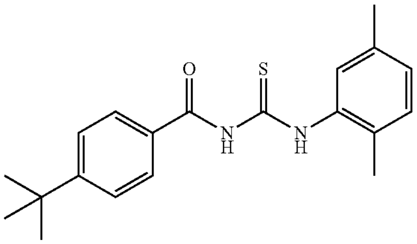 [SMILES: Cc1ccc(C)c(NC(=S)NC(=O)c2ccc(C(C)(C)C)cc2)c1] | C20H24N2OS | 4-tert-butyl-N-[(2,5-dimethylphenyl)-carbamothioyl]benzamide |
| 70 | 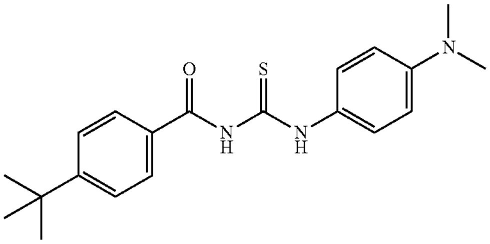 [SMILES: CN(C)c1ccc(NC(=S)NC(=O)c2ccc(C(C)(C)C)cc2)cc1] | C20H25N3OS HCl | 4-tert-butyl-N-[(4-dimethylaminophenyl)-carbamothioyl]benzamide hydrochloride |

TABLE 2-continued

| List of certain compounds of Formula I of the present invention. | | | |
|---|---|---|---|
| Compound | Chemical Structure | Molecular Formula | Chemical Name |
| 71 | 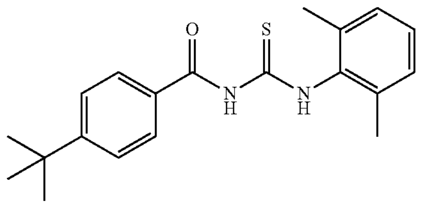 [SMILES: Cc1cccc(C)c1NC(=S)NC(=O)c1ccc(C(C)(C)C)cc1] | C20H24N2OS | 4-tert-butyl-N-[(2,6-dimethylphenyl)-carbamothioyl]benzamide |

The compounds of the invention include compounds which are of the following general Formula II or a pharmaceutically acceptable salt thereof:

Formula II

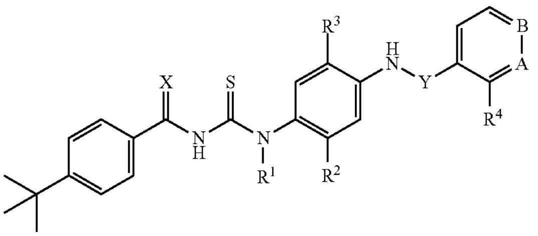

wherein X is selected from the group consisting of oxygen and NH;

Y is selected from the group consisting of: —$CH_2$—, —C(═O)—, —C(═S)— and —C(═NH)—;

A is selected from the group consisting of: N and $CR^5$;

B is selected from the group consisting of: N and $CR^6$;

$R^1$ is selected from the group consisting of: hydrogen and ethyl;

$R^2$ is selected from the group consisting of: hydrogen and chloro;

$R^3$ is selected from the group consisting of: hydrogen, methoxy, amino and hydroxyl;

$R^4$ is selected from the group consisting of: hydrogen, chloro and amino;

$R^5$ is selected from the group consisting of hydrogen and aminomethyl; and $R^6$ is selected from the group consisting of hydrogen, amino and aminomethyl.

Preferably, X is oxygen; Y is —$CH_2$— or —C(═O)—; A is C—H; B is C—H; $R^1$ is hydrogen; $R^2$ is hydrogen; $R^3$ is methoxy; $R^4$ is chloro; and each of $R^5$ and $R^6$ is hydrogen.

Preferably, the compound of Formula II is selected from the group consisting of: N-[4-[(4-tert-butylbenzoyl)-carbamothioylamino]-2-hydroxy-phenyl]-2-chloro-benzamide; 4-tert-butyl-N-[[4-[(2-chlorophenyl)-methylamino]-3-methoxy-phenyl]-carbamothioyl]-benzamide; N-[2-amino-4-[(4-tert-butylbenzoyl)-carbamothioylamino]-phenyl]-2-chloro-benzamide hydrochloride; N-[(4-benzamido-2-chloro-phenyl)carbamothioyl]-4-tert-butyl-benzamide; 4-tert-butyl-N-[[4-[(2-chlorobenzene-carbothioyl)amino]-3-methoxy-phenyl]-carbamothioyl]benzamide; 4-(aminomethyl)-N-[4-[(4-tert-butylbenzoyl)-carbamothioylamino]-2-methoxy-phenyl]benzamide hydrochloride; N-[4-[(4-tert-butylbenzene-carboximidoyl)-carbamothioylamino]-2-methoxy-phenyl]-2-chloro-benzamide; 4-tert-butyl-N-[[4-[(2-chlorobenzene-carboximidoyl)amino]-3-methoxy-phenyl]-carbamothioyl]benzamide; 3-(aminomethyl)-N-[4-[(4-tert-butylbenzoyl)-carbamothioylamino]-2-methoxy-phenyl]benzamide hydrochloride; 2-amino-N-[4-[(4-tert-butylbenzoyl)-carbamothioylamino]-2-methoxy-phenyl] benzamide; N-[4-[(4-tert-butylbenzoyl)-carbamothioylamino]-2-methoxy-phenyl]pyridine-3-carboxamide; N-[4-[(4-tert-butylbenzoyl)-carbamothioylamino]-2-methoxy-phenyl]pyridine-4-carboxamide; N-[[4-[(4-aminobenzoyl)amino]-3-methoxy-phenyl]-carbamothioyl]-4-tert-butyl-benzamide hydrochloride; N-[4-[(4-tert-butylbenzoyl)-carbamothioyl-ethyl-amino]-2-methoxy-phenyl]-2-chloro-benzamide; N-[4-[(4-tert-butylbenzoyl)-carbamothioylamino]-2-methoxy-phenyl]-2-chloro-benzamide; and N-[(4-benzamidophenyl)-carbamothioyl]-4-tert-butyl-benzamide.

More preferably, the compound of Formula II is N-[2-amino-4-[(4-tert-butylbenzoyl)-carbamothioylamino]-phenyl]-2-chloro-benzamide hydrochloride.

TABLE 3

| List of certain novel compounds of Formula II of the present invention. | | | | |
|---|---|---|---|---|
| Compound | Chemical Structure | Molecular Formula | Analytical Data | Chemical Name |
| 2 | 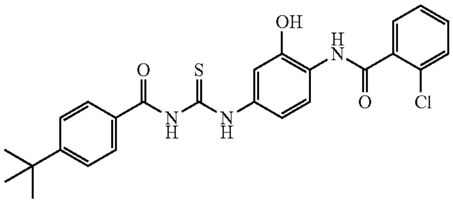 [SMILES: CC(C)(C)c1ccc(C(=O)NC(=S)Nc2ccc(NC(=O)c3ccccc3Cl)c(O)c2)cc1] | C25H24ClN3O3S | 1H NMR in DMSO-d6: δ 12.68 (s, 1H), 11.44 (s, 1H), 10.08 (s, 1H), 9.67 (s, 1H), 7.96 (d, 2H), 7.82 (d, 1H), 7.63 (dd, 1H), 7.54-7.59 (m, 3H), 7.43-7.52 (m, 3H), 7.08 (dd, 1H), 1.33 (s, 9H) | N-[4-[(4-tert-butylbenzoyl)-carbamothioylamino]-2-hydroxy-phenyl]-2-chloro-benzamide |

TABLE 3-continued

List of certain novel compounds of Formula II of the present invention.

| Compound | Chemical Structure | Molecular Formula | Analytical Data | Chemical Name |
|---|---|---|---|---|
| 3 | 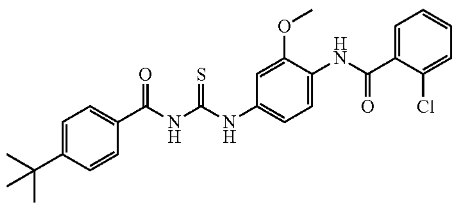 | C26H28ClN3O2S | 1H NMR in DMSO-d6: δ 12.52 (s, 1H), 11.27 (s, 1H), 7.93 (d, 2H), 7.55 (d, 2H), 7.45-7.7.47 (m, 1H), 7.23-7.37 (m, 4H), 6.98 (dd, 1H), 6.28 (d, 1H), 5.79 (t, 1H), 4.41 (d, 2H), 3.84 (s, 3H), 1.32 (s, 9H); Mass Spec: 481.9 $(M + H)^+$ | 4-tert-butyl-N-[[4-[(2-chlorophenyl)-methylamino]-3-methoxy-phenyl]-carbamothioyl]-benzamide |
| 6 | 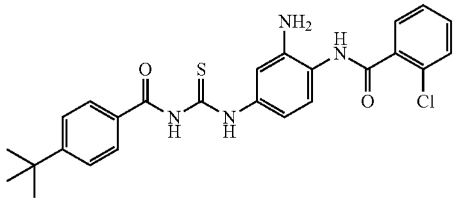 [SMILES: CC(C)(C)c1ccc(C(=O)NC(=S)Nc2ccc(NC(=O)c3ccccc3Cl)c(N)c2)cc1] | C25H25ClN4O2S HCl | 1H NMR in DMSO-d6: δ 12.63 (s, 1H), 11.38 (s, 1H), 9.85 (s, 1H), 7.95 (d, 2H), 7.68 (dd, 1H), 7.57 (d, 3H), 7.45-7.53 (m, 2H), 7.36 (d, 1H), 7.26 (s, 1H), 7.00 (dd, 1H), 3.68 (br, 3H), 1.33 (s, 9H); Mass Spec: 481.0 $(M + H)^+$; 503.0 $(M + Na)^+$ | N-[2-amino-4-[(4-tert-butylbenzoyl)-carbamothioylamino]-phenyl]-2-chloro-benzamide hydrochloride |
| 7 | 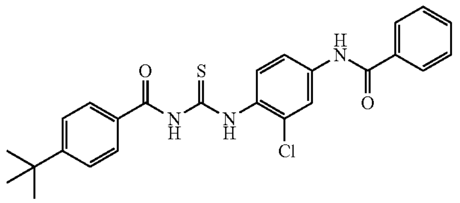 [SMILES: CC(C)(C)c1ccc(C(=O)NC(=S)Nc2ccc(NC(=O)c3ccccc3)cc2Cl)cc1] | C25H24ClN3O2S | 1H NMR in DMSO-d6: 12.65 (s, 1H), 11.67 (s, 1H), 10.48 (s, 1H), 8.12 (d, 1H), 7.96-7.99 (m, 5H), 7.76 (dd, 1H), 7.53-7.64 (m, 5H), 1.33 (s, 9H); Mass Spec: 466.2 $(M + H)^+$; 488.1 $(M + Na)^+$ | N-[(4-benzamido-2-chloro-phenyl)carbamothioyl]-4-tert-butyl-benzamide |
| 8 | 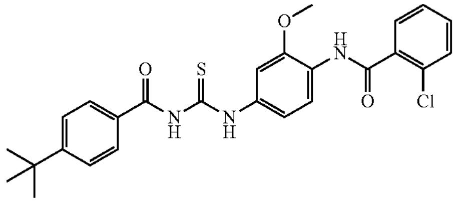 | C26H26ClN3O2S2 | 1H NMR in Pyridine-d5: δ 13.41 (s, 1H), 12.97 (s, 1H), 12.44 (s, 1H), 8.70 (d, 1H), 8.02-8.10 (m, 3H), 7.77 (dd, 1H), 7.63 (dd, 1H), 7.50 (d, 2H), 7.30 (dd, 1H), 7.08-7.26 (m, 2H), 3.70 (s, 3H), 1.24 (s, 9H); 13C NMR in CDCl3: δ 177.80, 166.88, 164.10, 157.90, 148.08, 135.35, 133.83, 131.63, 130.83, 130.48, 130.44, 128.62, 127.43, 127.23, 126.28, 126.06, 119.86, 116.26, 106.40, 56.15, 35.28, 31.04; Mass Spec: 512.0 $(M + H)^+$; 534.0 $(M + Na)^+$ | 4-tert-butyl-N-[[4-[(2-chlorobenzene-carbothioyl)amino]-3-methoxy-phenyl)-carbamothioyl]benzamide |
| 12 | 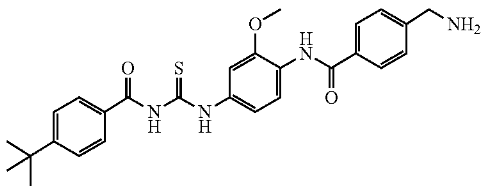 [SMILES: COc1cc(NC(=S)NC(=O)c2ccc(C(C)(C)C)cc2)ccc1NC(=O)c1ccc(CN)cc1] | C27H30N4O3S HCl | 1H NMR in DMSO-d6: δ 12.74 (s, 1H), 11.47 (s, 1H), 9.54 (s, 1H), 8.40 (br, 3H), 8.02 (d, 2H), 7.96 (d, 2H), 7.77 (d, 1H), 7.62 (d, 3H), 7.58 (d, 2H), 7.31 (dd, 1H), 4.13 (q, 2H), 3.86 (s, 3H), 1.33 (s, 9H); Mass Spec: 491.0 $(M + H)^+$; 513.0 $(M + Na)^+$ | 4-(aminomethyl)-N-[4-[(4-tert-butylbenzoyl)-carbamothioylamino]-2-methoxy-phenyl]benzamide hydrochloride |
| 23 | 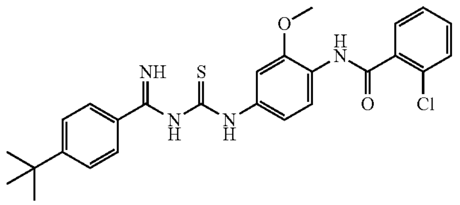 [SMILES: COc1cc(NC(=S)NC(=N)c2ccc(C(C)(C)C)cc2)ccc1NC(=O)c1ccccc1Cl] | C26H27ClN4O2S | 1H NMR in TFA-d1: δ 8.60 (br, 1H), 8.04 (s, 6H), 7.73-7.82 (m, 5H), 7.40 (br, 2H), 4.25 (s, 3H), 1.68 (s, 9H); Mass Spec: 495.1 $(M + H)^+$; 517.1 $(M + Na)^+$ | N-[4-[(4-tert-butylbenzene-carboximidoyl)-carbamothioylamino]-2-methoxy-phenyl]-2-chloro-benzamide |

TABLE 3-continued

List of certain novel compounds of Formula II of the present invention.

| Compound | Chemical Structure | Molecular Formula | Analytical Data | Chemical Name |
|---|---|---|---|---|
| 24 | 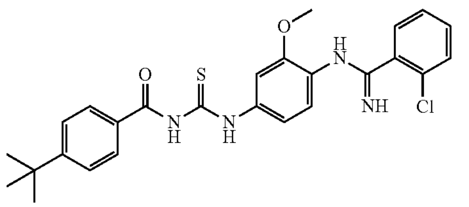 [SMILES: COc1cc(NC(=S)NC(=O)c2ccc(C(C)(C)C)cc2)ccc1NC(=N)c1ccccc1Cl] | C26H27ClN4O2S | 1H NMR in DMSO-d6: δ 12.67 (br, 1H), 10.13 (br, 1H), 9.66 (br, 1H), 8.24 (s, 1H), 7.93 (d, 2H), 7.56 (d, 2H), 7.25-7.49 (m, 5H), 6.74 (br, 1H), 3.71 (s, 3H), 1.32 (s, 9H); Mass Spec: 495.0 $(M + H)^+$ | 4-tert-butyl-N-[[4-[(2-chlorobenzene-carboximidoyl)amino]-3-methoxy-phenyl]-carbamothioyl]benzamide |
| 27 | 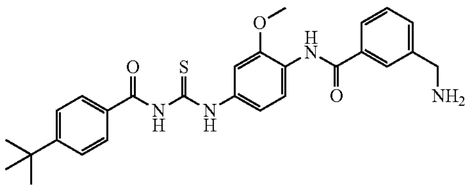 [SMILES: COc1cc(NC(=S)NC(=O)c2ccc(C(C)(C)C)cc2)ccc1NC(=O)c1cccc(CN)c1] | C27H30N4O3S HCl | 1H NMR in DMSO-d6: δ 12.74 (s, 1H), 11.48 (br, 1H), 9.51 (s, 1H), 8.25 (br, 3H), 8.09 (s, 1H), 8.01 (d, 1H), 7.97 (d, 2H), 7.78 (d, 1H), 7.68 (d, 1H), 7.57-7.61 (m, 4H), 7.31 (dd, 1H), 4.14 (s, 2H), 3.86 (s, 3H), 1.33 (s, 9H); Mass Spec: 491.0 $(M + H)^+$; 513.0 $(M + Na)^+$ | 3-(aminomethyl)-N-[4-[(4-tert-butylbenzoyl)-carbamothioylamino)-2-methoxy-phenyl]benzamide hydrochloride |
| 28 | 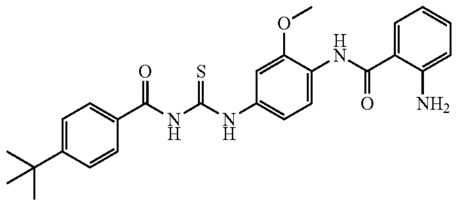 [SMILES: COc1cc(NC(=S)NC(=O)c2ccc(C(C)(C)C)cc2)ccc1NC(=O)c1ccccc1N] | C26H28N4O3S | 1H NMR in DMSO-d6: δ 12.73 (br, 1H), 11.45 (br, 1H), 9.22 (s, 1H), 7.96 (d, 2H), 7.79 (d, 1H), 7.65 (dd, 1H), 7.57 (d, 3H), 7.27 (dd, 1H), 7.21 (td, 1H), 6.76 (dd, 1H), 6.59 (td, 1H), 6.38 (s, 2H), 3.85 (s, 3H), 1.33 (s, 9H); Mass Spec: 477.0 $(M + H)^+$; 499.0 $(M + Na)^+$ | 2-amino-N-[4-[(4-tert-butylbenzoyl)-carbamothioylamino]-2-methoxy-phenyl]benzamide |
| 30 | 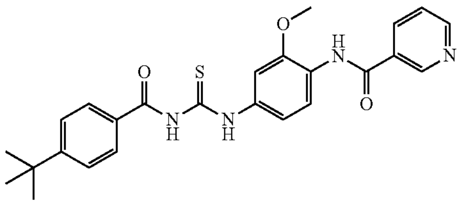 [SMILES: COc1cc(NC(=S)NC(=O)c2ccc(C(C)(C)C)cc2)ccc1NC(=O)c1cccnc1] | C25H26N4O3S | 1H NMR in DMSO-d6: δ 12.75 (s, 1H), 11.47 (s, 1H), 9.80 (s, 1H), 9.11 (d, 1H), 8.76 (dd, 1H), 8.30 (dt, 1H), 7.97 (d, 2H), 7.74 (d, 1H), 7.62 (d, 1H), 7.55-7.60 (3H), 7.31 (dd, 1H), 3.85 (s, 3H), 1.33 (s, 9H); Mass Spec: 463.0 $(M + H)^+$; 485.0 $(M + Na)^+$ | N-[4-[(4-tert-butylbenzoyl)-carbamothioylamino]-2-methoxy-phenyl]pyridine-3-carboxamide |
| 31 | 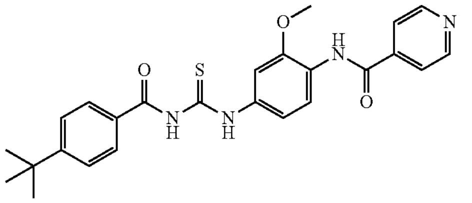 [SMILES: COc1cc(NC(=S)NC(=O)c2ccc(C(C)(C)C)cc2)ccc1NC(=O)c1ccncc1] | C25H26N4O3S | 1H NMR in CDCl3: δ 12.78 (s, 1H), 9.05 (s, 1H), 8.82 (d, 2H), 8.55 (d, 2H), 7 86 (d, 1H), 7.84 (d, 2H), 7.73 (dd, 2H), 7.57 (d, 2H), 7.16 (dd, 1H), 3.99 (s, 3H), 1.37 (s, 9H); Mass Spec: 463.0 $(M + H)^+$; 484.9 $(M + Na)^+$ | N-[4-[(4-tert-butylbenzoyl)-carbamothioylamino]-2-methoxy-phenyl]pyridine-4-carboxamide |
| 32 | 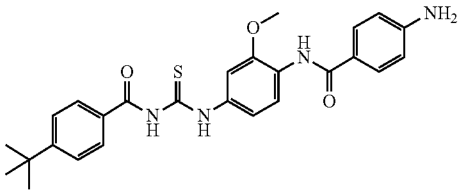 [SMILES: COc1cc(NC(=S)NC(=O)c2ccc(C(C)(C)C)cc2)ccc1NC(=O)c1ccc(N)cc1] | C26H28N4O3S HCl | 1H NMR in DMSO-d6: δ 12.72 (s, 1H), 11.44 (s, 1H), 9.00 (s, 1H), 7.96 (d, 2H), 7.88 (d, 1H), 7.73 (d, 2H), 7.56-7.58 (m, 3H), 7.25 (dd, 1H), 6.71 (d, 2H), 3.86 (s, 3H), 1.33 (s, 9H); Mass Spec: 477.0 $(M + H)^+$; 499.0 $(M + Na)^+$ | N-[[4-[(4-aminobenzoyl)amino]-3-methoxy-phenyl]-carbamothioyl]-4-tert-butyl-benzamide hydrochloride |
| 34 | 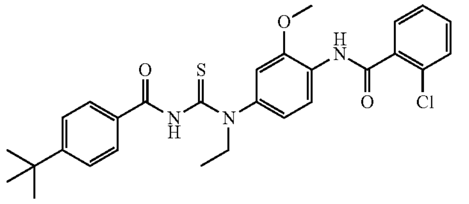 [SMILES: CCN(C(=S)NC(=O)c1ccc(C(C)(C)C)cc1)c1ccc(NC(=O)c2ccccc2Cl)c(OC)c1] | C28H30ClN3O3S | 1H NMR in DMSO-d6: δ 10.50 (s, 1H), 9.60 (s, 1H), 7.95 (d, 1H), 7.38-7.63 (m, 8H), 6.99 (s, 1H), 6.89 (d, 1H), 4.28 (br, 2H), 3.80 (s, 3H), 1.25 (s, 9H), 1.21 (t, 3H); Mass Spec: 524.0 $(M + H)^+$; 546.0 $(M + Na)^+$ | N-[4-[(4-tert-butylbenzoyl)-carbamothioyl-ethyl-amino]-2-methoxy-phenyl]-2-chloro-benzamide |

TABLE 4

| List of certain compounds of Formula II of the present invention. | | | |
|---|---|---|---|
| Compound | Chemical Structure | Molecular Formula | Chemical Name |
| 39 | 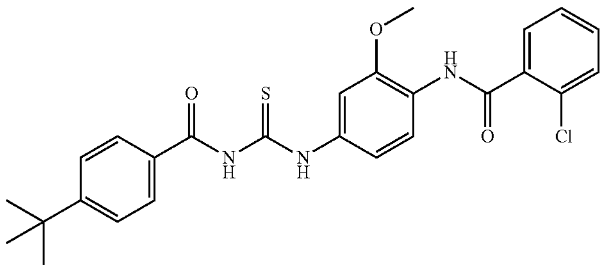 [SMILES: COc1cc(NC(=S)NC(=O)c2ccc(C(C)(C)C)cc2)ccc1NC(=O)c1ccccc1Cl] | C26H26ClN3O3S | N-[4-[(4-tert-butylbenzoyl)-carbamothioylamino]-2-methoxy-phenyl]-2-chloro-benzamide |
| 43 | 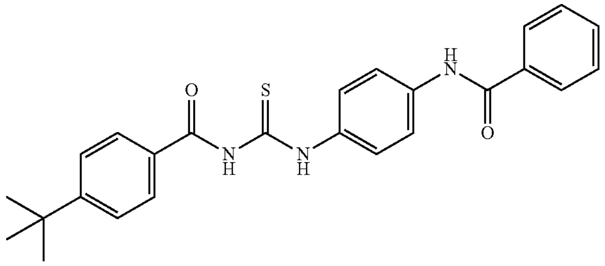 [SMILES: CC(C)(C)c1ccc(C(=O)NC(=S)Nc2ccc(NC(=O)c3ccccc3)cc2)cc1] | C25H25N3O2S | N-[(4-benzamidophenyl)-carbamothioyl]-4-tert-butyl-benzamide |

The compounds of the invention include compounds which are of the following general Formula III or a pharmaceutically acceptable salt thereof:

Formula III

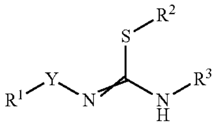

or

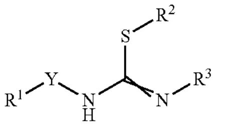

wherein Y is absent or is selected from the group consisting of: —$CH_2$—, —C(=O)—, —C(=S)— and —C(=NH)—;

$R^1$ is selected from the group consisting of aryl, cycloalkane and alkyl;

$R^2$ is alkyl; and $R^3$ is selected from the group consisting of: aryl, cycloalkane and alkyl.

Preferably, Y is —C(=O)—; $R^1$ is an aryl more preferably $R^1$ is selected from the group consisting of: substituted monocyclic, unsubstituted monocyclic, unsubstituted polycyclic and heteroaryl, most preferably $R^1$ is a substituted monocyclic aryl ring; $R^2$ is an alkyl selected from the group consisting of: $C_1$-$C_6$ branched alkyl, unbranched alkyl, substituted alkyl and unsubstituted alkyl, more preferably $R^2$ is an unbranched alkyl; $R^3$ is an aryl selected from the group consisting of: substituted aryl, unsubstituted monocyclic aryl, unsubstituted polycyclic aryl and heteroaryl, more preferably, $R^3$ is $C_3$-$C_7$ cycloalkane, $C_1$-$C_4$ branched or unbranched alkyl or a substituted aryl.

Preferably, the compound of Formula III is selected from the group consisting of: (NZ)-4-tert-butyl-N-[(2-chloro-5-methyl-anilino)-ethylsulfanyl-methylene]benzamide; N-[4-[[(Z)—N-(4-tert-butylbenzoyl)-C-ethylsulfanyl-carbonimidoyl]amino]-2-methoxy-phenyl]-2-chloro-benzamide; and (NZ)-4-tert-butyl-N-[(2-chloroanilino)-ethylsulfanyl-methylene]benzamide.

More preferably, the compound of Formula III is (NZ)-4-tert-butyl-N-[(2-chloro-5-methyl-anilino) -ethylsulfanyl-methylene]benzamide.

TABLE 5

| List of certain novel compounds of Formula III of the present invention. | | | | |
|---|---|---|---|---|
| Compound | Chemical Structure | Molecular Formula | Analytical Data | Chemical Name |
| 9 | 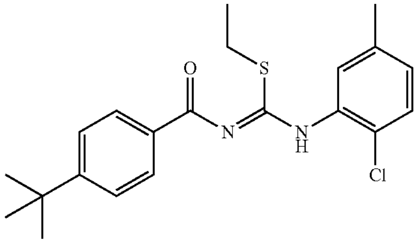 [SMILES: CCS/C(=N\C(=O)c1ccc(C(C)(C)C)cc1)Nc1cc(C)ccc1Cl] | C21H25ClN2OS | 1H NMR in CDCl3: δ 12.67 (s, 1H), 8.23 (br, 2H), 7.47 (d, 2H), 7.33-7.36 (m, 2H), 7.08 (br, 1H), 3.24 (q, 2H), 1.42 (t, 3H), 1.36 (s, 9H); Mass Spec: 388.9 $(M + H)^+$; 410.8 $(M + Na)^+$ | (NZ)-4-tert-butyl-N-[(2-chloro-5-methyl-anilino)-ethylsulfanyl-methylene]benzamide |

TABLE 5-continued

List of certain novel compounds of Formula III of the present invention.

| Compound | Chemical Structure | Molecular Formula | Analytical Data | Chemical Name |
|---|---|---|---|---|
| 10 | 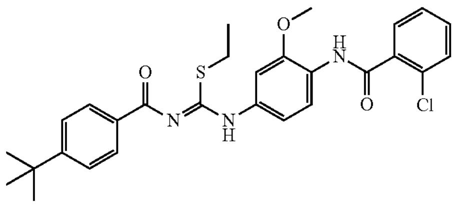 [SMILES: CCS/C(=N\C(=O)c1ccc(C(C)(C)C)cc1)Nc1ccc(NC(=O)c2ccccc2Cl)c(OC)c1] | C28H30ClN3O3S | 1H NMR in DMSO-d6: δ 11.41 (br, 1H), 9.69 (s, 1H), 8.05 (d, 2H), 7.94 (d, 1H), 7.41-7.61 (m, 6H), 7.23 (br, 1H), 7.08 (br, 1H), 3.79 (s, 3H), 3.08-3.17 (m, 2H), 1.25-1.35 (m, 12H); Mass Spec: 524.0 $(M + H)^+$; 545.9 $(M + Na)^+$ | N-[4-[[(Z)-N-(4-tert-butylbenzoyl)-C-ethylsulfanyl-carbonimidoyl]amino]-2-methoxy-phenyl]-2-chloro-benzamide |
| 14 | 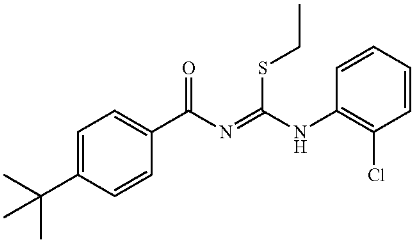 [SMILES: CCS/C(=N\C(=O)c1ccc(C(C)(C)C)cc1)Nc1ccccc1Cl] | C20H23ClN2OS | 1H NMR in DMSO-d6: δ 11.69 (br, 1/2H), 10.43 (br, 1/2H), 8.05 (br, 1H), 7.32-7.72 (m, 5H), 7.20 (br, 1H), 6.98 (br, 1H), 2.96-3.18 (m, 2H), 1.28-1.34 (m, 12H); Note: NH proton most likely switching between the 2 positions and reason for 2 signals at 11.69 and 10.43 ppm: Mass Spec: 375.0 $(M + H)^+$; 397.0 $(M + Na)^+$ | (NZ)-4-tert-butyl-N-[(2-chloroanilino)-ethylsulfanyl-methylene]benzamide |

The compounds of the invention also include each of the following compounds: 4-tert-butyl -N-[[4-[[5-(dimethylamino)-1-naphthyl]sulfonylamino]-3-methoxy-phenyl]-carbamothioyl]benzamide; N-[(3-aminophenyl)-carbamothioyl]-4-tert-butyl-benzamide; N-[(4-acetamido-3-methoxy-phenyl)-carbamothioyl]-4-tert-butyl-benzamide; 4-tert-butyl-N-[[3-methoxy -4-[5-(2-oxo-1,3,3a,4,6,6a-hexahydrothieno[3,4-d]imidazol-4-yl)-pentanoylamino] phenyl]-carbamothioyl]benzamide; 2-chloro-N-[4-(cyclohexanecarbonyl-carbamothioylamino) -2-methoxy-phenyl] benzamide; 2-chloro-N-[4-(ethylcarbamo-thioylamino) -2-methoxy-phenyl]benzamide; methyl 3-[4-[(4-tert-butylbenzoyl)carbamo-thioylamino]-2-methoxy-anilino]-3-oxo-propanoate; 4-tert-butyl-N-[(3-methoxy-4-ureido-phenyl) carbamothioyl]-benzamide; 4-tert-butyl-N-[[4-(4-pyridylamino)phenyl]-carbamothioyl]benzamide hydrochloride; N-[[4-[(4-tert-butylbenzoyl) amino]phenyl]carbamothioyl]-4-methyl-benzamide; 4-tert-butyl-N-[(5-tert-butyl-2-hydroxy-phenyl)-carbamothioyl]benzamide; 4-tert-butyl-N-(cyclohexyl-carbamothioyl) benzamide; 4-tert-butyl-N-[(4-methoxyphenyl)-carbamothioyl]benzamide; 4-tert-butyl -N-[(4-nitrophenyl)-carbamothioyl]benzamide; 4-tert-butyl-N-[(3-cyano-4,5-dimethyl-2-thienyl) -carbamothioyl] benzamide; 4-tert-butyl-N-(ethylcarbamothioyl)-benzamide; and N-[3-[(4-tert-butylbenzoyl)-carbamothioylamino]phenyl]-2-chloro-benzamide. Preferably, the compound is 4-tert-butyl-N-[[4-[[5-(dimethylamino)-1-naphthyl]sulfonylamino]-3-methoxy-phenyl]-carbamothioyl]benzamide. A preferred compound is N-[(4-acetamido-3-methoxy-phenyl) -carbamothioyl]-4-tert-butyl-benzamide.

TABLE 6

List of certain novel compounds of the present invention.

| Compound | Chemical Structure | Molecular Formula | Analytical Data | Chemical Name |
|---|---|---|---|---|
| 16 | 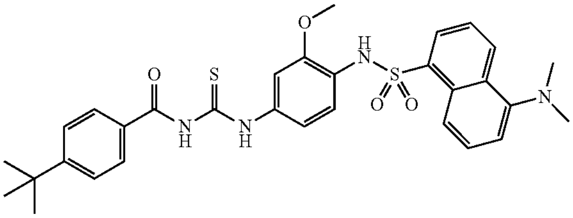 [SMILES: COc1cc(NC(=S)NC(=O)c2ccc(C(C)(C)C)cc2)ccc1NS(=O)(=O)c1cccc2c(N(C)C)cccc12] | C31H34N4O4S2 | 1H NMR in CDCl3: δ 12.63 (s, 1H) 8.98 (s, 1H), 8.49 (d, 1H), 8.36 (d, 1H), 8.17 (d, 1H), 7.79 (d, 2H), 7.53-7.58 (m, 3H), 7.43-7.47 (m, 3H), 7.18 (d, 1H), 6.98-7.02 (m, 1H), 3.41 (s, 3H), 2.87 (s, 6H), 1.35 (s, 9H) | 4-tert-butyl-N-[[4-[[5-(dimethylamino)-1-naphthyl] sulfonylamino]-3-methoxy-phenyl]-carbamothioyl] benzamide |
| 17 | 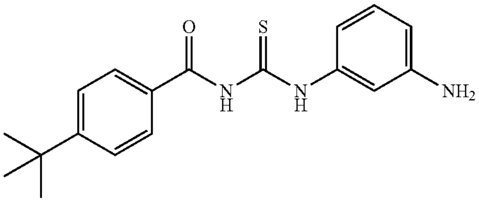 [SMILES: CC(C)(C)c1ccc(C(=O)NC(=S)Nc2cccc(N)c2)cc1] | C18H21N3OS | 1H NMR in $CDCl_3$: δ 12.57 (s, 1H), 9.00 (s, 1H), 7.82 (d, 2H), 7.55 (d, 2H), 7.27-7.28 (m, 1H), 7.19 (t, 1H), 7.03 (dd, 1H), 6.63 (dd, 1H), 1.36 (s, 9H); Mass Spec: 328.1 $(M + H)^+$ | N-[(3-aminophenyl)-carbamothioyl]-4-tert-butyl-benzamide |

TABLE 6-continued

List of certain novel compounds of the present invention.

| Compound | Chemical Structure | Molecular Formula | Analytical Data | Chemical Name |
|---|---|---|---|---|
| 20 | 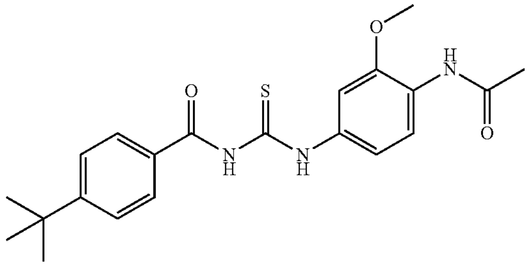 [SMILES: COc1cc(NC(=S)NC(=O)c2ccc(C(C)(C)C)cc2)ccc1NC(C)=O] | C21H25N3O3S | 1H NMR in DMSO-d6: δ 12.69 (s, 1H), 11.42 (s, 1H), 9.19 (s, 1H), 7.92-7.96 (m, 3H), 7.54-7.58 (m, 3H), 7.19 (dd, 1H), 3.84 (s, 3H), 2.09 (s, 3H), 1.32 (s, 9H); Mass Spec: 400.0 $(M + H)^+$; 422.0 $(M + Na)^+$ | N-[(4-acetamido-3-methoxy-phenyl)-carbamothioyl]-4-tert-butyl-benzamide |
| 25 | 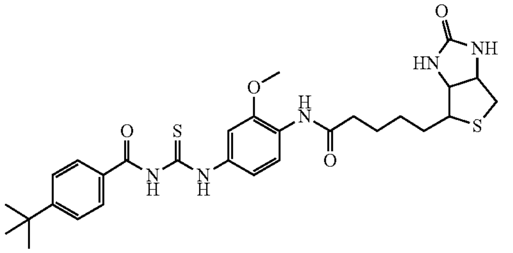 [SMILES: COc1cc(NC(=S)NC(=O)c2ccc(C(C)(C)C)cc2)ccc1NC(=O)CCCCC1SCC2NC(=O)NC21] | C29H37N5O4S2 | 1H NMR in CDCl3: δ 12.69 (s, 1H), 9.06 (s, 1H), 8.41 (d, 1H), 7.83 (d, 2H), 7.79 (s, 1H), 7.73 (s, 1H), 7.56 (d, 2H), 7.08 (d, 1H), 4.81 (s, 1H), 4.54 (s, 1H), 4.34 (m, 1H), 3.93 (s, 3H), 3.68 (s, 1H), 3.19 (br, 1H), 2.93 (m, 1H), 2.74 (d, 1H), 2.44 (m, 2H) 1.45-1.81 (m, 6H), 1.36 (s, 9H) | 4-tert-butyl-N-[[3-methoxy-4-[5-(2-oxo-1,3,3a,4,6,6a-hexahydrothieno[3,4-d]imidazol-4-yl)-pentanoylamino]phenyl]-carbamothioyl]benzamide |
| 26 | 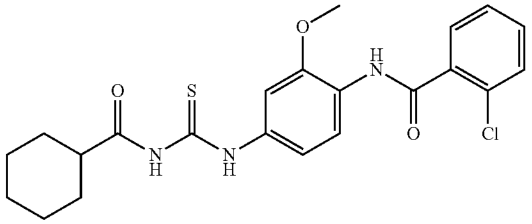 [SMILES: COc1cc(NC(=S)NC(=O)C2CCCCC2)ccc1NC(=O)c1ccccc1Cl] | C22H24ClN3O3S | 1H NMR in CDCl3: δ 12.50 (s, 1H), 8.57 (d, 1H), 8.57 (s, 1H), 8.52 (s, 1H), 7.78 (dd, 1H), 7.72 (d, 1H), 7.35-7.48 (m, 3H), 7.08 (dd, 1H), 3.90 (s, 3H), 2.24 (tt, 1H), 1.92-2.00 (m, 2H), 1.83-1.89 (m, 2H), 1.69-1.76 (m, 1H), 1.45-1.57 (m, 2H), 1.20-1.38 (3H); Mass Spec: 446.0 $(M + H)^+$; 467.9 $(M + Na)^+$ | 2-chloro-N-[4-(cyclo-hexanecarbonyl-carbamothioyl-amino)-2-methoxy-phenyl]benzamide |
| 33 | 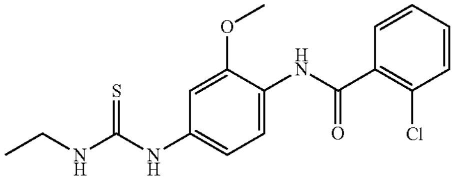 [SMILES: CCNC(=S)Nc1ccc(NC(=O)c2ccccc2Cl)c(OC)c1] | C17H18ClN3O2S | 1H NMR in CDCl3: δ 8.60 (d, 1H), 8.58 (s, 1H), 7.79 (dd, 1H), 7.56 (br, 1H), 7.38-7.49 (m, 3H), 6.90 (dd, 1H), 6.77 (d, 1H), 6.01 (br, 1H), 3.89 (s, 3H), 3.68 (q, 2H), 1.20 (t, 3H); Mass Spec: 363.9 $(M + H)^+$; 386.0 $(M + Na)^+$ | 2-chloro-N-[4-(ethylcarbamo-thioylamino)-2-methoxy-phenyl]benzamide |
| 35 | 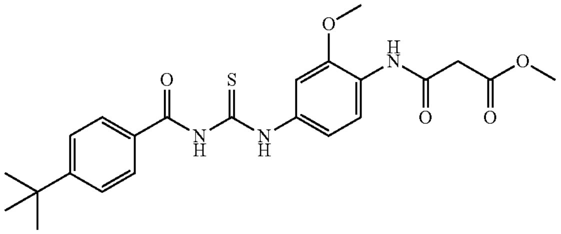 [SMILES: COC(=O)CC(=O)Nc1ccc(NC(=S)NC(=O)c2ccc(C(C)(C)C)cc2)cc1OC] | C23H27N3O5S | 1H NMR in DMSO-d6: δ 12.70 (s, 1H), 11.43 (s, 1H), 9.58 (s, 1H), 7.94-8.03 (m, 3H), 7.56-7.58 (m, 3H), 7.21 (d, 1H), 3.86 (s, 3H), 3.66 (s, 3H), 3.62 (s, 2H), 1.32 (s, 9H); Mass Spec: 458.0 $(M + H)^+$; 480.0 $(M + Na)^+$ | methyl 3-[4-[(4-tert-butylbenzoyl)carbamo-thioylamino]-2-methoxy-anilino]-3-oxo-propanoate |
| 37 | 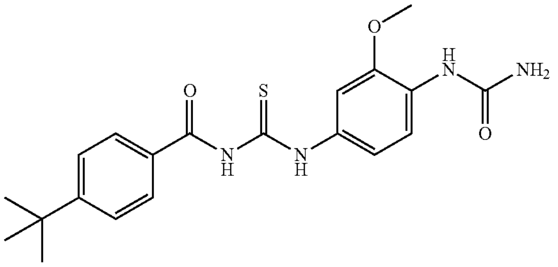 [SMILES: COc1cc(NC(=S)NC(=O)c2ccc(C(C)(C)C)cc2)ccc1NC(N)=O] | C20H24N4O3S | 1H NMR in DMSO-d6: δ 12.65 (br, 1H), 11.37 (br, 1H), 8.09 (d, 1H), 8.00 (s, 1H), 7.95 (d, 2H), 7.56 (d, 2H), 7.50 (d, 1H), 7.10 (dd, 1H), 6.21 (s, 2H), 3.85 (s, 3H), 1.32 (s, 9H); Mass Spec: 401.0 $(M + H)^+$; 423.0 $(M + Na)^+$ | 4-tert-butyl-N-[(3-methoxy-4-ureido-phenyl)carbamothioyl]-benzamide |

TABLE 6-continued

List of certain novel compounds of the present invention.

| Compound | Chemical Structure | Molecular Formula | Analytical Data | Chemical Name |
|---|---|---|---|---|
| 38 | 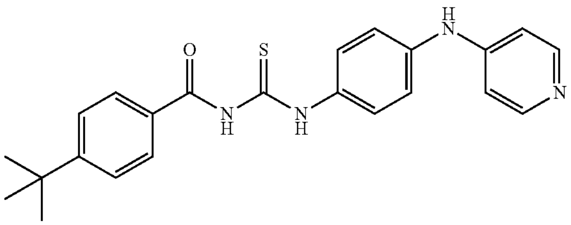 [SMILES: CC(C)(C)c1ccc(C(=O)NC(=S)Nc2ccc(Nc3ccncc3)cc2)cc1] | C23H24N4OS HCl | 1H NMR in DMSO-d6: δ 12.76 (s, 1H), 11.58 (s, 1H), 8.52 (s, 2H), 8.49 (d, 2H), 7.95-7.99 (m, 4H), 7.72 (d, 2H), 7.58 (d, 2H), 6.98 (d, 2H), 1.33 (s, 9H), Mass Spec: 405.1 $(M + H)^+$ | 4-tert-butyl-N-[[4-(4-pyridylamino) phenyl]-carbamothioyl] benzamide hydrochloride |

TABLE 7

List of certain compounds of the present invention.

| Compound | Chemical Structure | Molecular Formula | Chemical Name |
|---|---|---|---|
| 41 | 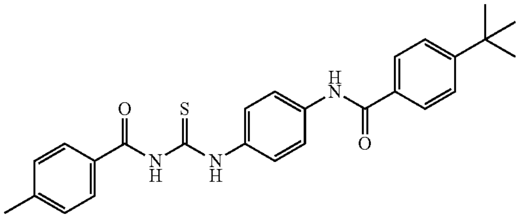 [SMILES: Cc1ccc(C(=O)NC(=S)Nc2ccc(NC(=O)c3ccc(C(C)(C)C)cc3)cc2)cc1] | C26H27N3O2S | N-[[4-[(4-tert-butylbenzoyl)amino]phenyl]carbamothioyl]-4-methyl-benzamide |
| 46 | 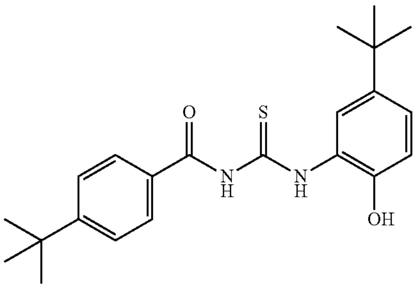 [SMILES: CC(C)(C)c1ccc(C(=O)NC(=S)Nc2cc(C(C)(C)C)ccc2O)cc1] | C22H28N2O2S | 4-tert-butyl-N-[(5-tert-butyl-2-hydroxy-phenyl)-carbamothioyl]benzamide |
| 64 | 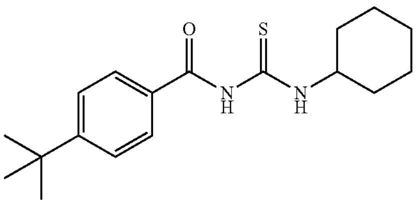 [SMILES: CC(C)(C)c1ccc(C(=O)NC(=S)NC2CCCCC2)cc1] | C18H26N2OS | 4-tert-butyl-N-(cyclohexyl-carbamothioyl)benzamide |
| 68 | 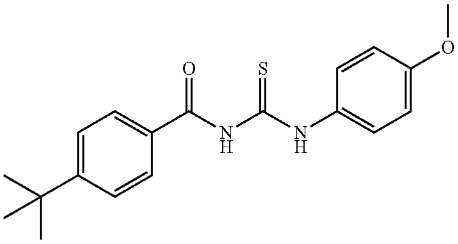 [SMILES: COc1ccc(NC(=S)NC(=O)c2ccc(C(C)(C)C)cc2)cc1] | C19H22N2O2S | 4-tert-butyl-N-[(4-methoxyphenyl)-carbamothioyl]benzamide |

TABLE 7-continued

| List of certain compounds of the present invention. | | | |
|---|---|---|---|
| Compound | Chemical Structure | Molecular Formula | Chemical Name |
| 69 | 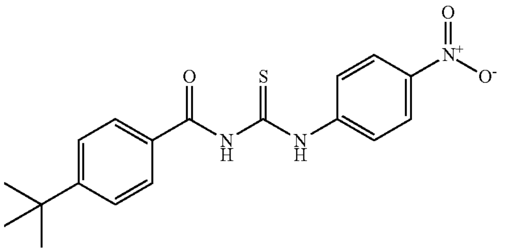 [SMILES: CC(C)(C)c1ccc(C(=O)NC(=S)Nc2ccc([N+](=O)[O-])cc2)cc1] | C18H19N3O3S | 4-tert-butyl-N-[(4-nitrophenyl)-carbamothioyl]benzamide |
| 72 | 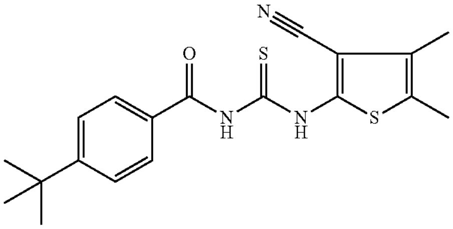 [SMILES: Cc1sc(NC(=S)NC(=O)c2ccc(C(C)(C)C)cc2)c(C#N)c1C] | C19H21N3OS2 | 4-tert-butyl-N-[(3-cyano-4,5-dimethyl-2-thienyl)-carbamothioyl]benzamide |
| 73 | 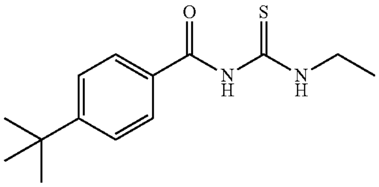 [SMILES: CCNC(=S)NC(=O)c1ccc(C(C)(C)C)cc1] | C14H20N2OS | 4-tert-butyl-N-(ethylcarbamothioyl)-benzamide |
| 74 | | C25H24ClN3O2S | N-[3-[(4-tert-butylbenzoyl)-carbamothioylamino]phenyl]-2-chloro-benzamide |

The method of the present invention is for the treatment or prophylaxis of a viral or bacterial infection or disease associated therewith, comprising administering in a therapeutically effective amount to a mammal in need thereof, any of the compounds described above.

Preferably, the mammal is a human. Also preferably, the viral infection is caused by a virus family selected from the group consisting of: Bunyaviridae, Poxviridae, Arenaviridae, Picornaviridae, Togaviridae, Flaviviridae, Filoviridae, Paramyxoviridae, Orthomyxoviridae and Retroviridae.

In one embodiment of the invention, the viral infection is a Bunyaviridae infection preferably caused by a virus selected from the group consisting of Rift Valley fever virus, La Crosse virus and Andes virus.

In another embodiment of the invention, the viral infection is a Poxviridae infection preferably caused by a virus selected from the group consisting of the vaccinia virus and monkeypox virus.

In yet another embodiment of the invention, the viral infection is an Arenaviridae infection preferably caused by a virus selected from the group consisting of Tacaribe virus and lymphocytic choriomeningitis virus.

In another embodiment of the invention, the viral infection ds a Picornaviridae infection preferably caused by Encephalomyocarditis virus.

In yet another embodiment of the invention, the viral infection is a Togaviridae infection preferably caused by Sindbis virus.

In yet another embodiment of the invention, the viral infection is a Flaviviridae infection preferably caused by a virus selected from the group consisting of Dengue virus, West Nile virus, yellow fever virus, Japanese encephalitis virus, and tick-borne encephalitis virus. Most preferably, the flavivirus is a Dengue virus selected from the group consisting of DEN-1, DEN-2, DEN-3, and DEN-4. In yet another embodiment of the invention, the viral infection is associated with a condition selected from the group consisting of Dengue fever, Yellow fever, West Nile, St. Louis encephalitis, Hepatitis C, Murray Valley encephalitis, and Japanese encephalitis. Most preferably, the viral infection is associated with Dengue fever wherein said Dengue fever is selected from the group consisting of classical dengue fever, dengue hemorrhagic fever syndrome, and dengue shock syndrome.

In yet another embodiment of the invention, the viral infection is a Filoviridae infection preferably caused by a virus selected from the group consisting of Ebola virus and Zaire strain.

In yet another embodiment of the invention, the viral infection is an Orthomyxoviridae infection preferably caused by an influenza virus, preferably the H1N1 virus.

In yet another embodiment of the invention, the viral infection is caused by a Retroviridae infection preferably caused by a Human Immunodeficiency virus.

The method of the present invention may also comprise co-administration of: a) other antivirals such as Ribavirin or cidofovir; b) vaccines; and/or c) interferons or pegylated interferons.

Preferably, the bactaerial infection is caused by a bacteria family selected from the group consisting of Chlamydiaceae and Coxiellaceae.

In one embodiment, the bacterial infection is a Chlamydiaceae infection preferably caused by bacteria selected from the group consisting of *Chlamydophila caviae* and *Chlamydophila muridarum.*

In another embodiment of the invention, the bacterial infection is a Coxiellaceae infection preferably caused by *Coxiella burnetti* bacteria.

TABLE 8

Pathogen families and human diseases associated therewith.

| Pathogen Family | Human Disease Associated with Pathogen Family |
|---|---|
| Bunyaviridae | Hemorrhagic fever, retinal vasculitis, encephalitis, hemorrhagic fever with renal syndrome (HFRS), hantavirus pulmonary syndrome(HPS) |
| Poxviridae | Family members include causative agents of smallpox and monkeypox. |
| Arenaviridae | Hemorrhagic fever |
| Picornaviridae | Common cold, Poliovirus, Hand-Foot-and-Mouth Disease, Hepatitis A. |
| Togaviridae | Encephalitis, arthritic disease, Rubella |
| Flaviviridae | Dengue hemorrhagic fever, Dengue shock syndrome |
| Filoviridae | Hemorrhagic fever |
| Paramyxoviridae | Mumps, measles, pneumonia, bronchitis |
| Orthomyxoviridae | Influenza |
| Retroviridae | AIDS, cancer |
| Chlamydiaceae | Chlamydia |
| Coxiellaceae | Q fever |

Definitions

In accordance with this detailed description, the following abbreviations and definitions apply. It must be noted that as used herein, the singular forms "a," "an," and "the" include plural referents unless the context clearly dictates otherwise.

The publications discussed herein are provided solely for their disclosure. Nothing herein is to be construed as an admission regarding antedating the publications. Further, the dates of publication provided may be different from the actual publication dates, which may need to be independently confirmed.

Where a range of values is provided, it is understood that each intervening value is encompassed. The upper and lower limits of these smaller ranges may independently be included in the smaller, subject to any specifically-excluded limit in the stated range. Where the stated range includes one or both of the limits, ranges excluding either both of those included limits are also included in the invention. Also contemplated are any values that fall within the cited ranges.

Unless defined otherwise, all technical and scientific terms used herein have the same meaning as commonly understood by one of ordinary skill in the art. Any methods and materials similar or equivalent to those described herein can also be used in practice or testing. All publications mentioned herein are incorporated herein by reference to disclose and describe the methods and/or materials in connection with which the publications are cited.

By "patient" or "subject" is meant to include any mammal. A "mammal," for purposes of treatment, refers to any animal classified as a mammal, including but not limited to, humans, experimental animals including rats, mice, and guinea pigs, domestic and farm animals, and zoo, sports, or pet animals, such as dogs, horses, cats, cows, and the like.

The term "efficacy" as used herein refers to the effectiveness of a particular treatment regime. Efficacy can be measured based on change of the course of the disease in response to an agent.

The term "success" as used herein in the context of a chronic treatment regime refers to the effectiveness of a particular treatment regime. This includes a balance of efficacy, toxicity (e.g., side effects and patient tolerance of a formulation or dosage unit)', patient compliance, and the like. For a chronic administration regime to be considered "successful" it must balance different aspects of patient care and efficacy to produce a favorable patient outcome.

The terms "treating," "treatment," and the like are used herein to refer to obtaining a desired pharmacological and physiological effect. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment," as used herein, covers any treatment of a disease in a mammal, such as a human, and includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; and (c) relieving the disease, i.e., causing regression of the disease and/or its symptoms or conditions. Treating a patient's suffering from disease related to pathological inflammation is contemplated. Preventing, inhibiting, or relieving adverse effects attributed to pathological inflammation over long periods of time and/or are such caused by the physiological responses to inappropriate inflammation present in a biological system over long periods of time are also contemplated.

As used herein, "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkylamino" refers to the group —NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkyl" refers to linear or branched alkyl groups having from 1 to 10 carbon atoms, alternatively 1 to 6 carbon atoms. This term is exemplified by groups such as methyl, t-butyl, n-heptyl, octyl and the like.

"Amino" refers to the group —$NH_2$.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one, and the like) provided that the point of attachment is through an aromatic ring atom.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$S(O)_2$-alkyl, —$S(O)_2$-substituted alkyl, —$S(O)_2$-cycloalkyl, —$S(O)_2$-substituted cycloalkyl, —$S(O)_2$-alkenyl, —$S(O)_2$-substituted alkenyl, —$S(O)_2$-aryl, —$S(O)_2$-substituted aryl, —$S(O)_2$-heteroaryl, —$S(O)_2$-substituted heteroaryl, —$S(O)_2$-heterocyclic, —$S(O)_2$-substituted heterocyclic, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OS(O)_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and diheterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2NRR$ where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclohexyl, cyclooctyl and the like. Excluded from this definition are multi-ring alkyl groups such as adamantanyl, etc.

"Halo" or "halogen" refers to fluoro, chloro, bromo and iodo.

"Heteroaryl" refers to an aromatic carbocyclic group of from 2 to 10 carbon atoms and 1 to 4 heteroatoms selected from the group consisting of oxygen, nitrogen and sulfur within the ring or oxides thereof. Such heteroaryl groups can have a single ring (e.g., pyridyl or furyl) or multiple condensed rings (e.g., indolizinyl or benzothienyl) wherein one or more of the condensed rings may or may not be aromatic provided that the point of attachment is through an aromatic ring atom. Additionally, the heteroatoms of the heteroaryl group may be oxidized, i.e., to form pyridine N-oxides or 1,1-dioxo-1,2,5-thiadiazoles and the like. Additionally, the carbon atoms of the ring may be substituted with an oxo (═O). The term "heteroaryl having two nitrogen atoms in the heteroaryl, ring" refers to a heteroaryl group having two, and only two, nitrogen atoms in the heteroaryl ring and optionally containing 1 or 2 other heteroatoms in the heteroaryl ring, such as oxygen or sulfur.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$S(O)_2$-alkyl, —$S(O)_2$-substituted alkyl, —$S(O)_2$-cycloalkyl, —$S(O)_2$-substituted cycloalkyl, —$S(O)_2$-alkenyl, —$S(O)_2$-substituted alkenyl, —$S(O)_2$-aryl, —$S(O)_2$-substituted aryl, —$S(O)_2$-heteroaryl, —$S(O)_2$-substituted heteroaryl, —$S(O)_2$-heterocyclic, —$S(O)_2$-substituted heterocyclic, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —NRS $(O)_2$—NR-alkyl, —$NRS(O)_2$—NR-substituted alkyl, —$NRS(O)_2$—NR-aryl, —$NRS(O)_2$—NR— substituted aryl, —$NRS(O)_2$—NR-heteroaryl, —$NRS(O)_2$—NR— substituted heteroaryl, —$NRS(O)_2$—NR-heterocyclic, —NRS $(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and diheterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2$NRR where R is hydrogen or alkyl.

"Sulfonyl" refers to the group —$S(P)_2$R where R is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Optionally substituted" means that the recited group may be unsubstituted or the recited group may be substituted.

"Pharmaceutically-acceptable carrier" means a carrier that is useful in preparing a pharmaceutical composition or formulation that is generally safe, non-toxic, and neither biologically nor otherwise undesirable, and includes a carrier that is acceptable for veterinary use as well as human pharmaceutical use.

"Pharmaceutically-acceptable cation" refers to the cation of a pharmaceutically-acceptable salt.

"Pharmaceutically-acceptable salt" refers to salts which retain the biological effectiveness and properties of compounds which are not biologically or otherwise undesirable. Pharmaceutically-acceptable salts refer to pharmaceutically-acceptable salts of the compounds, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Pharmaceutically-acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri (iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

Pharmaceutically-acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

A compound may act as a pro-drug. Pro-drug means any compound which releases an active parent drug in vivo when such pro-drug is administered to a mammalian subject. Pro-drugs are prepared by modifying functional groups present in such a way that the modifications may be cleaved in vivo to release the parent compound. Pro-drugs include compounds wherein a hydroxy, amino, or sulfhydryl group is bonded to any group that may be cleaved in vivo to regenerate the free hydroxyl, amino, or sulfhydryl group, respectively. Examples of pro-drugs include, but are not limited to esters (e.g., acetate, formate, and benzoate derivatives), carbamates (e.g., N,N-dimethylamino-carbonyl) of hydroxy functional groups, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically-effective amount" means the amount of a compound that, when administered to a mammal for treating a disease, is sufficient to effect such treatment for the disease. The "therapeutically-effective amount" will vary depending on the compound, the disease, and its severity and the age, weight, etc., of the mammal to be treated.

Pharmaceutical Formulations of the Compounds

In general, compounds will be administered in a therapeutically-effective amount by any of the accepted modes of administration for these compounds. The compounds can be administered by a variety of routes, including, but not limited to, oral, parenteral (e.g., subcutaneous, subdural, intravenous, intramuscular, intrathecal, intraperitoneal, intracerebral, intraarterial, or intralesional routes of administration), topical, intranasal, localized (e.g., surgical application or surgical suppository), rectal, and pulmonary (e.g., aerosols, inhalation, or powder). Accordingly, these compounds are effective as both injectable and oral compositions. The compounds can be administered continuously by infusion or by bolus injection.

The actual amount of the compound, i.e., the active ingredient, will depend on a number of factors, such as the severity of the disease, i.e., the condition or disease to be treated, age, and relative health of the subject, the potency of the compound used, the route and form of administration, and other factors.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compounds lies within a range of circulating concentrations that include the $ED_{50}$ with little or no toxicity. The dosage may vary within this range depending upon the dosage form employed and the route of administration utilized. For any compound used, the therapeutically-effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically-effective dose." Amounts effective for this use will depend on the disease condition being treated as well as by the judgment of the attending clinician depending upon factors such as the severity of the inflammation, the age, weight, and general condition of the patient, and the like.

The compositions administered to a patient are in the form of pharmaceutical compositions described supra. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. It will be understood that use of certain of the foregoing excipients, carriers, or stabilizers will result in the formation of pharmaceutical salts.

The active compound is effective over a wide dosage range and is generally administered in a pharmaceutically- or therapeutically-effective amount. The therapeutic dosage of the compounds will vary according to, for example, the particular use for which the treatment is made, the manner of administration of the compound, the health and condition of the patient, and the judgment of the prescribing physician. For example, for intravenous administration, the dose will typically be in the range of about 0.5 mg to about 100 mg per kilogram body weight. Effective doses can be extrapolated from dose-response curves derived from in vitro or animal model test systems. Typically, the clinician will administer the compound until a dosage is reached that achieves the desired effect.

When employed as pharmaceuticals, the compounds are usually administered in the form of pharmaceutical compositions. Pharmaceutical compositions contain as the active ingredient one or more of the compounds above, associated with one or more pharmaceutically-acceptable carriers or excipients. The excipient employed is typically one suitable for administration to human subjects or other mammals. In making the compositions, the active ingredient is usually mixed with an excipient, diluted by an excipient, or enclosed within a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained, or delayed-release of the active ingredient after administration to the patient by employing procedures known in the art.

The quantity of active compound in the pharmaceutical composition and unit dosage form thereof may be varied or adjusted widely depending upon the particular application, the manner or introduction, the potency of the particular compound, and the desired concentration. The term "unit dosage forms" refers to physically-discrete units suitable as unitary dosages for human subjects and other mammals, each unit containing a predetermined quantity of active material calculated to produce the desired therapeutic effect, in association with a suitable pharmaceutical excipient.

The compound can be formulated for parenteral administration in a suitable inert carrier, such as a sterile physiological saline solution. The dose administered will be determined by route of administration.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s). Also, the manufacture of the formulation should be cost-effective. All of these factors ultimately determine the overall success and usefulness of an intravenous formulation.

Other accessory additives that may be included in pharmaceutical formulations and compounds as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is able to maintain a formulation pH in the range of 4 to 8. Generally, a 1:1 to 10:1 mole ratio of buffer (where the moles of buffer are taken as the combined moles of the buffer ingredients, e.g., sodium citrate and citric acid) to drug is used.

A useful buffer is sodium citrate/citric acid in the range of 5 to 50 mg per ml. sodium citrate to 1 to 15 mg per ml. citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

An intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 2000 mg of the active ingredient.

The tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically-acceptable, aqueous or organic solvents, or mixtures thereof, and powders. The liquid or solid compositions may contain suitable pharmaceutically-acceptable excipients as described supra. Compositions in pharmaceutically-acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered from devices which deliver the formulation in an appropriate manner.

The compounds can be administered in a sustained release form. Suitable examples of sustained-release preparations include semipermeable matrices of solid hydrophobic polymers containing the compounds, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly(vinyl alcohol)), polylactides (U.S. Pat. No. 3,773, 919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e., injectable microspheres composed of lactic acid-glycolic acid copolymer and leuprolide acetate), and poly-D-(−)-3-hydroxybutyric acid (EP 133, 988).

The compounds can be administered in a sustained-release form, for example a depot injection, implant preparation, or osmotic pump, which can be formulated in such a manner as to permit a sustained-release of the active ingredient. Implants for sustained-release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated by the host.

Transdermal delivery devices ("patches") may also be employed. Such transdermal patches may be used to provide continuous or discontinuous infusion of the compounds in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on-demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid-soluble and amenable to transportation across the blood-brain barrier. Alternatively, the delivery of hydrophilic drugs may be enhanced by intra-arterial infusion of hypertonic solutions which can transiently open the blood-brain barrier.

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

Pharmaceutical compositions are suitable for use in a variety of drug delivery systems. Suitable formulations for use in the present invention are found in *Remington's Pharmaceutical Sciences*, Mace Publishing Company, Philadelphia, Pa., 17th ed. (1985).

In the examples below, if an abbreviation is not defined above, it has its generally accepted meaning. Further, all temperatures are in degrees Celsius (unless otherwise indicated). The following Methods were used to prepare the compounds set forth below as indicated.

EXAMPLE 1

Formulation 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

EXAMPLE 2

Formulation 2

A tablet formula is prepared using the ingredients below:

| Ingredient | Quantity (mg/capsule) |
|---|---|
| Active ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

EXAMPLE 3

Formulation 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

EXAMPLE 4

Formulation 4

Tablets, each containing 30 mg of active ingredient, are prepared as follows:

| Ingredient | Quantity (mg/capsule) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium Carboxymethyl starch | 4.5 mg |

-continued

| Ingredient | Quantity (mg/capsule) |
|---|---|
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules, which after mixing, are compressed on a tablet machine to yield tablets each weighing 150 mg.

EXAMPLE 5

Formulation 5

Capsules, each containing 40 mg of medicament, are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

EXAMPLE 6

Formulation 6

Suppositories, each containing 25 mg of active ingredient, are made as follows:

| Ingredient | Amount |
|---|---|
| Active Ingredient | 25 mg |
| Saturated fatty acids glycerides | to 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 7

Formulation 7

Suspensions, each containing 50 mg of medicament per 5.0 ml dose, are made as follows:

| Ingredient | Amount |
|---|---|
| Active ingredient | 50.0 mg |
| Xanthan gum | 4.0 mg |
| Sodium carboxymethyl cellose (11%) Microcrystalline cellulose (89%) | 500 mg |
| Sucrose | 1.75 g |
| Sodium benzoate | 10.0 mg |
| Flavor and color | q.v. |
| Purified water | to 5.0 ml |

The medicament, sucrose, and xanthan gum are blended, passed through a NO. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 8

Formulation 8

Hard gelatin tablets, each containing 15 mg of active ingredient, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

EXAMPLE 9

Formulation 9

An intravenous formulation may be prepared as follows:

| Ingredient | (mg/capsule) |
|---|---|
| Active Ingredient | 250.0 mg |
| Isotonic saline | 1000 ml |

Therapeutic compound compositions generally are placed into a container having a sterile access port, for example, an intravenous solution bag or vial having a stopper pierceable by a hypodermic injection needle or similar sharp instrument.

EXAMPLE 10

Formulation 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

EXAMPLE 11

Formulation 11

An aerosol formulation may be prepared as follows: A solution of the candidate compound in 0.5% sodium bicarbonate/saline (w/v) at a concentration of 30.0 mg/mL is prepared using the following procedure:

Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:

1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

Preparation of 30.0 mg/mL Candidate Compound: 10.0 mL

| Ingredient | Gram/100.0 mL | Final Concentration |
|---|---|---|
| Candidate Compound | 0.300 g | 30.0 mg/mL |
| .05% Sodium Bicarbonate/Saline Stock Solution | q.s. ad 10.0 mL | q.s. ad 100% |

Procedure:

1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix.

EXAMPLE 12

Synthesis of 4-tert-butyl-N-[[2-chloro-4-(methylamino)phenyl]-carbamothioyl]benzamide hydrochloride (Compound 5)

4-tert-butyl-N-[[2-chloro-4-(methylamino)phenyl]-carbamothioyl]benzamide hydrochloride (Compound 5) was synthesized according to the following scheme:

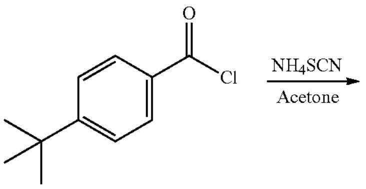

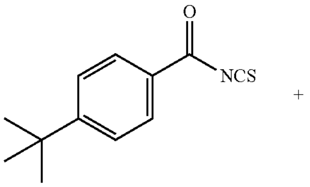

Intermediate A

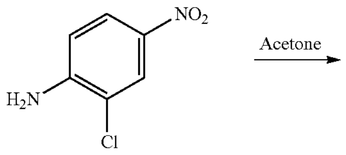

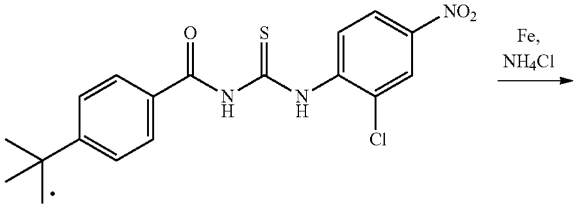

5.1

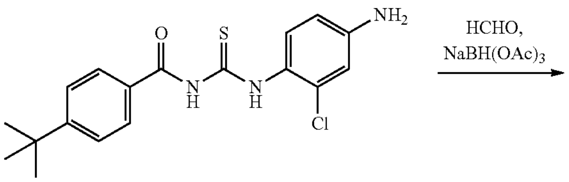

5.2

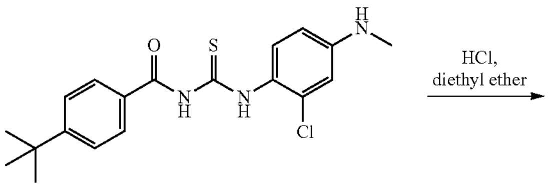

5.3

-continued

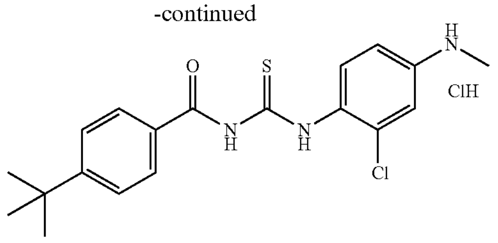

5

Synthesis of 4-tert-butylbenzoyl isothiocyanate (Intermediate A)

To a stirred solution of 4-tert-butylbenzoyl chloride (6 g, 198 mmol) in acetone (250 mL) was added ammonium thiocynate (28 g, 237 mmol). The resulting yellow suspension was stirred at room temperature for 2 hours, condensed to dryness and then reconstituted through the addition of ethyl acetate (200 mL). The organic portion was washed with a saturated sodium bicarbonate solution (2×200 ml) and brine (200 mL). The resulting organic phase was dried over anhydrous sodium sulfate and concentrated to a sticky liquid. The residue was chilled in a −10° C. freezer to give 37 grams of Intermediate A as a yellow solid (88%).

Synthesis of 4-tert-butyl-N-[(2-chloro-4-nitro-phenyl)carbamothioyl]benzamide (compound 5-1)

To a stirred solution of intermediate A (5.85 g, 24.6 mmol) in acetone (120 mL) was added 2-chloro-4-nitroanaline (4.25 g, 24.6 mmol) in one portion. The resulting yellow solution was stirred at room temperature for 36 hours, condensed and purified via normal phase column chromatography using a solvent system of 0-10% ethyl acetate in hexanes to yield 8.6 g of compound 5-1 as a yellow solid (89%).

Synthesis of N-[(4-amino-2-chloro-phenyl)carbamothioyl]-4-tert-butyl-benzamide (compound 5-2)

To a stirred solution of compound 5-1 (8.6 g, 22 mmol) in acetonitrile (200 mL) was added ammonium chloride (17.6 g, 330 mmol) and water (100 mL). To the resulting light yellow suspension was added iron powder (18.5 g, 330 mmol) which resulted in a dark green mixture. After stirring for 24 hours, the reaction was filtered through a pad of Celite and the filter cake was washed with ethyl acetate. The organic portion of the filtrate was removed and the aqueous portion was extracted twice with ethyl acetate. The combined organic portions were washed with brine and dried over anhydrous sodium sulfate. The resulting solution was concentrated to dryness to yield 6.6 g of compound 5-2 as a yellow solid (83%).

Synthesis of 4-tert-butyl-N-[[2-chloro-4-(methylamino)phenyl]carbamothioyl]benzamide (compound 5-3)

To a stirred solution of compound 5-2 (1.60 g, 4.4 mmol) in tetrahydrofuran (100 mL) was added formaldehyde (37% aqueous, 0.4 mL, 4.8 mmol), sodium triacetoxyborohydride (0.6 mL, 17.6 mmol) and acetic acid (0.5 mL, 8.8 mmol). The resulting yellow suspension was stirred at room temperature for 36 hours. The reaction mixture was diluted with dichloromethane (200 mL) and washed with a saturated sodium bicarbonate solution and brine. The organic layer was concentrated and then purified via normal phase column chromatography using 0-5% ethyl acetate in dichloromethane to yield 530 mg of compound 5-3 as a yellow solid (32%).

Synthesis of 4-tert-butyl-N-[[2-chloro-4-(methylamino)phenyl]carbamothioyl]benzamide hydrochloride (compound 5)

To an ice-water bath cooled solution of 5-3 (200 mg, 0.53 mmol) in dichloromethane (6 mL) was added 2M HCl in diethyl ether (0.35 mL, 0.69 mmol). The resulting red solution was stirred at room temperature for 30 minutes. After removing solvents, the material was dried under high vacuum to yield 210 mg of compound 5 as a yellow solid (96%).

Example 13

Synthesis of 4-tert-butyl-N-[[4-[(2-chlorophenyl)-methylamino]-3-methoxy-phenyl]-carbamothioyl]-benzamide (Compound 3)

4-tert-butyl-N-[[4-[(2-chlorophenyl)-methylamino]-3-methoxy-phenyl]-carbamothioyl]-benzamide (compound 3) was synthesized according to the following scheme:

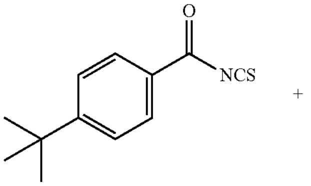

Intermediate A

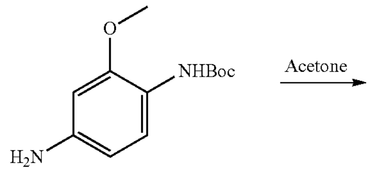

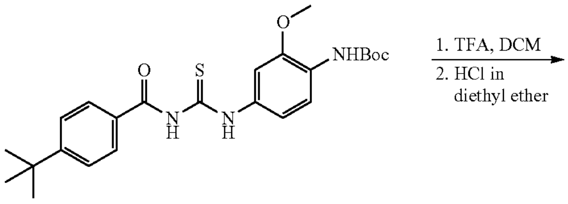

3.1

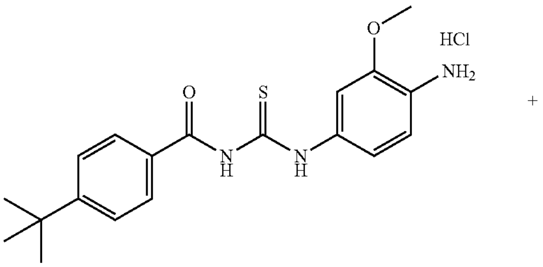

3-2

-continued

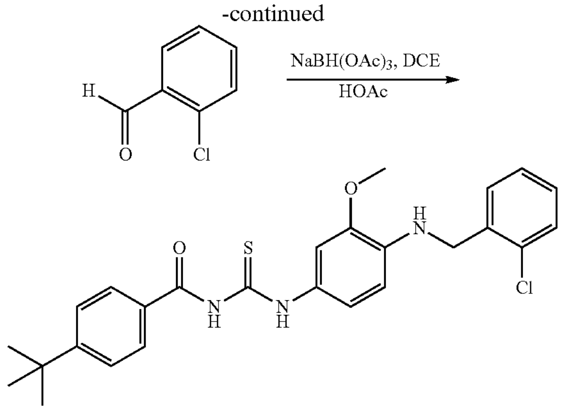

3

Synthesis of tert-butyl N-[4-[(4-tert-butylbenzoyl) carbamothioylamino]-2-methoxy-phenyl]carbamate (compound 3-1)

To a solution of intermediate A (see Example 12; 1.8 g, 8.22 mmol) in acetone (30 mL) was added (4-Amino-2-methoxy-phenyl)-carbamic acid tert-butyl ester (1.95 g, 8.22 mmol). The reaction mixture was stirred at room temperature for 16 hours, concentrated to dryness and treated with ethyl acetate (200 mL). The organic portion was washed with water and a brine solution followed by evaporation of solvent. The residue was purified by normal phase column chromatography utilizing 10-50% ethyl acetate in hexanes to provide 2.41 g of compound 3-1 as a pale white solid (64%).

Synthesis of N-[(4-amino-3-methoxy-phenyl)carbamothioyl]-4-tert-butyl-benzamide hydrochloride (compound 3-2)

A solution of compound 3-1 (12 g, 26.2 mmol) in anhydrous dichloromethane (180 mL) was cooled to 0° C. To the reaction mixture was added a solution of trifluoroacetic acid (20 mL, 262 mmol) in dichloromethane (70 mL). After stirring at room temperature for 16 hours, the solvent was removed and the residue was co-evaporated with anhydrous acetonitrile. The remaining oil was treated with diethyl ether followed by the addition of 2.0M HCl in diethyl ether (15 mL). The solution was stirred at room temperature for 2 hours and then concentrated to provide a white solid. The solid was washed with copious amounts of diethyl ether to afford 9.2 g of compound 3-2 as a white solid (89%).

Synthesis of 4-tert-butyl-N-[[4-[(2-chlorophenyl) methylamino]-3-methoxy-phenyl]carbamothioyl] benzamide (compound 3)

To a solution of compound 3-2 (150 mg, 0.381 mmol) in dichloromethane (4 mL) was added 2-chlorobenzaldehyde (54 mg, 0.572 mmol). The solution was stirred at room temperature for 1 hour followed by the addition of triacetoxyborohydride (121 mg, 0.572 mmol). After stirring the suspension for 18 hours at room temperature, the reaction was quenched by the addition of a saturated sodium bicarbonate solution (3 mL) and concentrated. The residue was treated with ethyl acetate, washed with brine and dried over anhydrous sodium sulfate. After removing solvents, the residue was purified by normal phase column chromatography eluting 15-45% ethyl acetate in hexanes to yield 35 mg of compound 3 as a yellow solid (19%).

EXAMPLE 14

Synthesis of N-[2-amino-4-[(4-tert-butylbenzoyl)-carbamothioylamino]-phenyl]-2-chloro-benzamide hydrochloride (compound 6)

N-[2-amino-4-[(4-tert-butylbenzoyl)-carbamothioylamino]-phenyl]-2-chloro-benzamide hydrochloride was synthesized according to the following scheme:

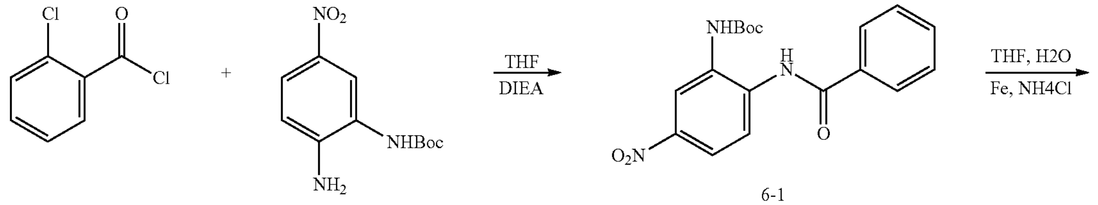

6-1

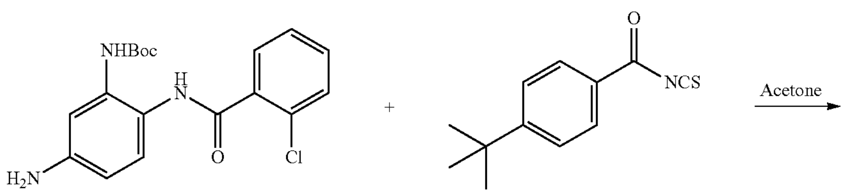

6-2

Intermediate A

-continued

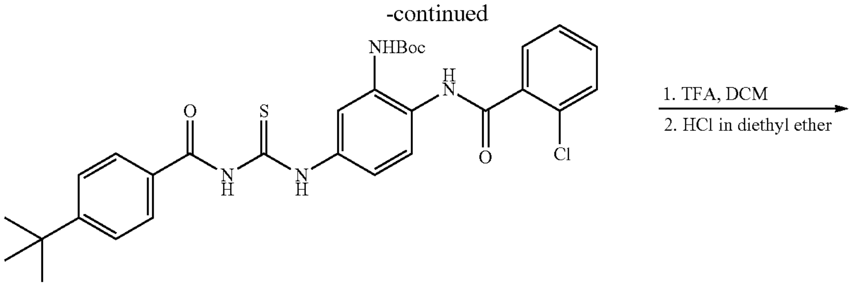

6-3

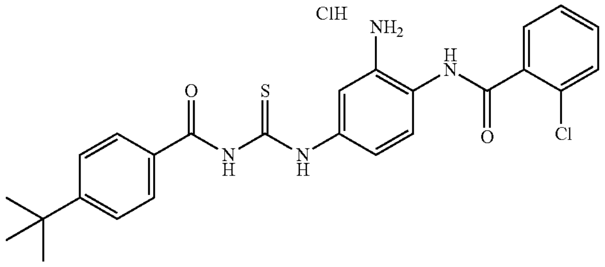

6

Synthesis of tert-butyl N-(2-benzamido-5-nitrophenyl)carbamate (compound 6-1)

To a solution of 2-chlorobenzoyl chloride (100 μL, 0.789 mmol) and diisopropylethylamine (165 μL, 0.947 mmol) in tetrahydrofuran (8 mL) at 0° C. was added 4-nitrobenzene-1,2-diamine (200 mg, 0.789 mmol) drop wise. The reaction was allowed to warm to room temperature and stir for 3 hours. The reaction mixture was concentrated and the resulting residue was purified by normal phase column chromatography utilizing 75% hexanes in ethyl acetate to produce 452 mg of compound 6-1 as a solid after vacuum drying (>99%).

Synthesis of tert-butyl N-(5-amino-2-benzamidophenyl)carbamate (compound 6-2)

To a solution of compound 6-1 (0.452 g, 0.789 mmol) in tetrahydrofuan (5 mL) was added a saturated ammonium chloride solution (3 mL) followed by iron powder (220 mg, 3.95 mmol). The reaction was stirred for 72 hours and then filtered through Celite. The filtrate was concentrated and the resulting residue was purified by normal phase column chromatography using 0.5-1% methanol in, dichloromethane to produce 152 mg of compound 6-2 as a solid (53%).

Synthesis of tert-butyl N-[5-[(4-tert-butylbenzoyl)carbamothioylamino]-2-[(2-chlorobenzoyl)amino]phenyl]-carbamate (compound 6-3)

To a solution of compound 6-2 (99.7 mg, 0.42 mmol) in acetone (8 mL) was added intermediate A (see Example 12; 152 mg, 0.42 mmol). The reaction was stirred for 2 hours at room temperature and then concentrated. The resulting residue was purified by normal phase column chromatography eluting 75% hexanes in ethyl acetate to produce 238 mg of compound 6-3 as a solid (97%).

Synthesis of N-[2-amino-4-[(4-tert-butylbenzoyl)carbamothioylamino]phenyl]-2-chloro-benzamide hydrochloride (6)

To a solution of compound 6-3 (237 mg, 0.40 mmol) in dichloromethane (2 mL) at 0° C. under argon was added a 50% solution of trifluoroacetic acid in dichloromethane (8 mL). The reaction was stirred for 3 hours at room temperature and then concentrated. The residue was dissolved in dimethylformamide and purified by prep-HPLC to afford 148 mg of a solid following vacuum drying. A solution of 79 mg of the free base was dissolved in dichloromethane (2 mL) and cooled with an ice-water bath followed by the slow addition of 2.0M HCl in diethyl ether (2 mL). The mixture was evaporated immediately to afford 74 mg of compound 6 as a brown solid (88%).

EXAMPLE 15

Synthesis of 4-tert-butyl-N-[(2-chloro-5-methylanilino)-ethylsulfanyl-methylene]benzamide (compound 9)

4-tert-butyl-N-[(2-chloro-5-methyl-anilino)-ethylsulfanyl-methylene]benzamide was synthesized according to the following scheme:

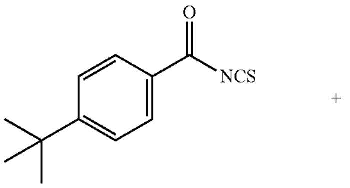

Intermediate A

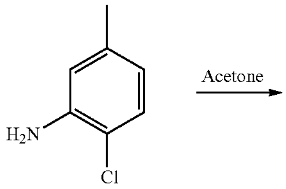

-continued

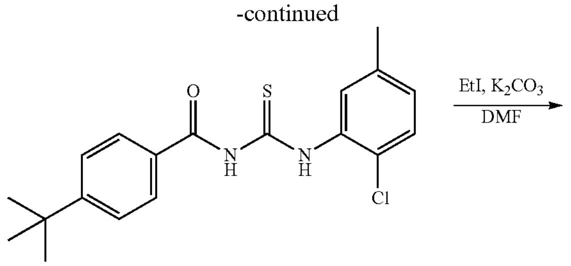

9-1

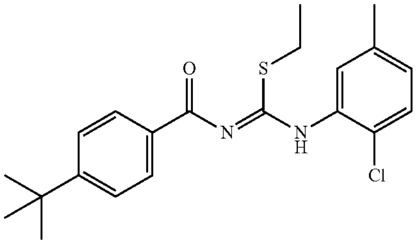

9

Synthesis of 4-tert-butyl-N-[(2-chloro-5-methyl-phenyl)carbamothioyl]benzamide (compound 9-1)

To a solution of 2-chloro-5-methylphenylamine (72.8 mg, 0.514 mmol) in acetone (3 mL) was added a solution of intermediate A (see Example 12; 122 mg, 0.556 mmol) in acetone (3 mL). The reaction was stirred at room temperature for 2 hours and then concentrated. The resulting residue was purified by normal phase column chromatography eluting 85% hexanes in ethyl acetate to yield 187 mg of compound 9-1 as a solid following vacuum drying (>99%).

Synthesis of 4-tert-butyl-N-[(2-chloro-5-methyl-anilino)-ethylsulfanylmethylene]benzamide (compound 9)

To a solution of compound 9-1 (150 mg, 0.42 mmol) in dimethylformamide (4 mL) was added potassium carbonate (72 mg, 0.52 mmol) followed by iodoethane (65 mg, 0.42 mmol). The reaction mixture was stirred at room temperature for 4 hours. After the reaction period, the mixture was diluted with ethyl acetate (50 mL), washed with brine (2×15 mL) and water (15 mL), dried over anhydrous sodium sulfate and concentrated under reduced pressure. The crude material was purified by normal phase column chromatography using a gradient elution of 100 to 98% hexanes in ethyl acetate to produce 60 mg of compound 9 as a white powder (36%).

EXAMPLE 16

Summary of the Biological Assays Used

Assay Development

Sensitive and reproducible high throughput screening (HTS) assays were established to measure cytopathic effect induced by infection with either Rift Valley fever virus (RVFV) or La Crosse virus (LACV), viruses that represent two distinct genera in the genetically diverse Bunyaviridae family. To determine the amount of LACV stock required to produce complete CPE, Vero cell monolayers were seeded on 96-well plates and infected with 2-fold serial dilutions of the LACV stock. At 3, 4, or 5 days post-infection, replicate cultures were fixed with 5% glutaraldehyde and stained with 0.1% crystal violet. Virus-induced cytopathic effect (CPE) was quantified spectrophotometrically at OD570. From this analysis, a 1:20,000 dilution of LACV stock (MOI of 0.01 pfu/cell) was chosen for use in the HTS assay, and the optimum time of infection at this dilution prior to fixation and crystal violet staining was determined to be 4 days. A CPE assay used to measure CPE caused by the RVFV vaccine strain MP-12 (provided by ViroPharma, Inc.) was similarly optimized using Vero cells and a 1:12,000 dilution of RVFV stock (0.03 PFU/cell).

Virus Stocks

RVFV vaccine strain MP12 and LACV were provided by ViroPharma, Inc. Virus stocks were prepared in BHK-21 cells infected at low multiplicity (0.01 plaque forming units (PFU)/cell) and harvested when at the time of maximum CPE. The samples were frozen and thawed to release cell-associated virus. The cell debris was removed by low-speed centrifugation, and the resulting virus suspension was stored in 1 ml aliquots at −80° C. The titer of the virus suspension was quantified by standard assay on Vero cells.

Primary HTS Screening

The LACV and RVFV CPE assays were used to identify antiviral compounds from the SIGA chemical library capable of inhibiting both LACV-induced and RVFV-induced CPE. Each evaluation run consisted of 48×96-well plates with 80 compounds per plate to generate 3,840 data points per run per virus, and each run incorporated ribavirin controls ($EC_{50}$ value 0.75 mM for LACV and 0.3 mM for RVFV). Compounds were dissolved in DMSO and diluted in medium such that the final concentration in each well was 5 μM compound and 0.5% DMSO. The compounds were added robotically to the culture medium using the PerkinElmer MultiPROBE® II HT PLUS robotic system. Following compound addition, cultures were infected with LACV or RVFV as above. After 4 days incubation, plates were processed and the CPE quantified on a PerkinElmer EnVision II plate reader system.

The results of these experiments indicated that the 96-well assay format is robust and reproducible. The S/B ratio (ratio of signal of cell control wells (signal) to virus control wells (background)) has averaged 9.0±1.8. The well-to-well variability was determined for each individual plate and found to have a coefficient of variance of less than 15% for both positive control and negative control wells, and overall assay-to-assay variability was less than 15%. Taken together, these results show that a sensitive and reproducible HTS assay has been successfully developed to evaluate our compound library for inhibitors of LACV and RVFV replication.

Virus Yield Assay

Vero cells were seeded onto 24-well plates in complete media and inclubated overnight at 37° C. The following day, compounds were added to triplicate wells of the plate across a range of concentrations between 25 μM and 0.1 nM. Control wells lacking virus or containing DMSO vehicle only were also prepared in triplicate. Wells were then infected with Tacaribe virus at an MOI of 0.01 and incubated for 72 hours at 37° C. Supernantants harvested at 72 hours from each well were serially diluted ($10^{-1}$ to $10^{-5}$) and each dilution was plated onto a fresh monolayer of Vero cells in duplicate, and overlayed with 3 ml of 1.1% SeaPlaque agarose in media (MEM+5% FBS+P/S). Cells were incubated for 7 days at 37° C. Following incubation, cells were fixed with 5% gluteraldehyde and stained with 0.1% crystal violet. Viral plaques counted were used to calculate yield reduction as compared to cells treated with DMSO vehicle.

Inhibitory Potency

Chemically tractable hits identified in either the LACV or the RVFV primary screens were subsequently tested for potency against both LACV and RVFV in cell culture. This secondary screen serves to confirm the result from the primary assay, determine the effective dose range of the compound, and identify any compounds from the individual primary screens that have broad spectrum activity against both RVFV and LACV. Dose response curves are generated by measuring virus replication in the presence of a range of compound concentrations. Typically, eight compound concentrations are used (25, 8, 2.56, 0.81, 0.26, 0.084, 0.027 and 0.009 μM) in order to generate inhibition curves suitable for calculating $EC_{50}$ values. Compounds that have $EC_{50}$ values<25 μM against both LACV and RVFV were further evaluated for selectivity.

Inhibitory Selectivity

To determine if compounds are selective for inhibition of virus replication and not simply toxic to cells, cytotoxicity of each hit that produces $EC_{50}$ values<10 μM is determined by an Alamar Blue fluorometric method, which measures the in situ reduction of resazurin (7-hydroxy-3H-phenoxazin-3-one 10-oxide) by mitochondrial enzymes in metabolically active cells. The Alamar Blue assay is used to generate dose response curves and the cytotoxic concentration that kills 50% of cells ($CC_{50}$) is determined. Cells are seeded at subconfluent densities in order to identify compounds that may be cytostatic.

Spectrum of Activity

Hits that were potent and selective against both RVFV and LACV were tested in additional ongoing antiviral HTS programs at SIGA against a spectrum of pathogens from different viral and bacterial families. Testing for in vitro antiviral activity was performed using clinically relevant members of multiple virus families including vaccinia virus and monkeypox virus (Poxviridae), tacaribe virus and lymphocytic choriomeningitis virus (Arenaviridae), encephalomyocarditis virus (Picornaviridae), Sindbis virus (Togaviridae), dengue fever virus (Flaviviridae), Ebola virus (Filoviridae), Andes virus (Bunyaviridae), respiratory syncytial virus (Paramyxoviridae), influenza virus (Orthomyxoviridae) human immunodeficiency virus (Retroviridae). CPE assays for vaccinia virus, Sindbis virus and encephalomyocarditis virus were carried out in a manner similar to that described for LACV and RVFV. Antiviral activities against Ebola virus, human immunodeficiency virus, lymphocytic choriomeningitis virus, and dengue virus were assessed using virus yield assays similar to that described for tacaribe virus. MIC values for compounds 1, 2, and 3 against *Chlamydophila caviae* were determined using a fluorescent marker to label intracellular bacterial growth in cell culture. Briefly, compounds were delivered in media to Vero cells across a range of concentrations (25, 8, 2.56, 0.81, 0.26, 0.084, 0.027 and 0.0075 μM). Cells were then inoculated with *C. caviae* at a multiplicity of infection of 0.8. Infected cells were centrifuged for 40 min (1200 rpm, 37° C.) and then incubated in a standard cell culture incubator for 20 hours. At this point media were removed from each well and a fluorescent tracker of host Golgi metabolism (NBD C6-ceramide, Molecular Probes cat # N1154: 1 μg/ml in PBS) was added to the cells. NBD-C6-ceramide traffics to intracellular *Chlamydia* within infected cells and the abundance of label can be measured using fluorescein or GFP channels on a fluorimeter or fluorescent microscope. The label was incubated on cells for 30 min in the cell culture incubator and then replaced with MEM-10. After 3 hr in the incubator, medium was removed and replaced with PBS. The development of *Chlamydia* in cells was quantified by fluorescent measurement of retained label, and by visual evaluation of the infected cells. For influenza virus EC50 determination, A549 cells were plated in flat bottom, 96-well plates. Compounds were delivered in media to A549 cells across a range of concentrations (25, 8, 2.56, 0.81, 0.26, 0.084, 0.027 and 0.0075 μM). Cells were then inoculated with influenza virus in media containing 4 μg/ml TPCK-treated trypsin and incubated at 37 C for 72 hours. Following incubation, 25 ul of supernatant from infected wells was transferred to a separate, white, 96-well assay plate. 75 μl of MUNANA neuraminidase substrate (20 mM in EMEM-0) was added to each well. Plates were incubated at 37 C for 1 hour and 100 μl of stop solution was added to each well. Plates were read at excitation wavelength of 360 nM and emission wavelength of 465 nM.

EXAMPLE 17

Determining Anti-Viral and Anti-Bacterial Activity of Compounds of the Invention The spectrum of activity of various compounds of the present invention against a broad range of viral and intracellular bacterial targets was measured as indicated above and is shown in Tables 9-15 below.

TABLE 9

Anti-Viral and Anti-Bacterial Activity of certain novel compounds of Formula I of the present invention.

| Compound | Avg Activity (VV)<br>A: EC50 ≤ 1 μM;<br>B: 1 < EC50 ≤ 10 μM;<br>C: 10 < EC50 ≤ 25 μM;<br>D: >25 μM | Avg Activity (LACV)<br>A: EC50 ≤ 1 μM;<br>B: 1 < EC50 ≤ 10 μM;<br>C: 10 < EC50 ≤ 25 μM;<br>D: >25 μM<br>n.d.: not determined | Avg Activity (*C. Caviae*)<br>A: EC50 ≤ 1 μM;<br>B: 1 < EC50 ≤ 10 μM;<br>C: 10 < EC50 ≤ 25 μM;<br>D: >25 μM;<br>n.d.: not determined | Misc Activity<br>A: EC50 ≤ 1 μM;<br>B: 1 < EC50 ≤ 10 μM;<br>C: 10 < EC50 ≤ 25 μM;<br>D: >25 μM;<br>n.d.: not determined |
|---|---|---|---|---|
| 1 | A | A | A | Influenza: A |
| 4 | A | A | A | n.d. |
| 5 | A | A | A | n.d. |
| 11 | A | B | A | Dengue: A<br>Influenza: B<br>Ebola: n.d.<br>MPX: n.d. |
| 13 | B | A | A | n.d. |
| 15 | B | A | A | n.d. |
| 18 | B | B | A | Dengue: A<br>Tacaribe: A |

TABLE 9-continued

Anti-Viral and Anti-Bacterial Activity of certain novel compounds of Formula I of the present invention.

| Compound | Avg Activity (VV)<br>A: EC50 ≤ 1 μM;<br>B: 1 < EC50 ≤ 10 μM;<br>C: 10 < EC50 ≤ 25 μM;<br>D: >25 μM | Avg Activity (LACV)<br>A: EC50 ≤ 1 μM;<br>B: 1 < EC50 ≤ 10 μM;<br>C: 10 < EC50 ≤ 25 μM;<br>D: >25 μM<br>n.d.: not determined | Avg Activity (*C. Caviae*)<br>A: EC50 ≤ 1 μM;<br>B: 1 < EC50 ≤ 10 μM;<br>C: 10 < EC50 ≤ 25 μM;<br>D: >25 μM;<br>n.d.: not determined | Misc Activity<br>A: EC50 ≤ 1 μM;<br>B: 1 < EC50 ≤ 10 μM;<br>C: 10 < EC50 ≤ 25 μM;<br>D: >25 μM;<br>n.d.: not determined |
|---|---|---|---|---|
| | | | | Ebola: n.d.<br>MPX: n.d. |
| 19 | B | B | A | n.d. |
| 21 | B | B | A | Dengue: A<br>Tacaribe: A<br>Influenza: A<br>Ebola: n.d.<br>MPX: n.d. |
| 22 | B | B | A | n.d. |
| 29 | B | D | n.d. | n.d. |
| 36 | C | D | A | n.d. |

TABLE 10

Anti-Viral and Anti-Bacterial Activity of certain compounds of Formula I of the present invention.

| Compound | Avg Activity (VV)<br>A: $EC_{50}$ ≤ 1 μM;<br>B: 1 < $EC_{50}$ ≤ 10 μM;<br>C: 10 < $EC_{50}$ ≤ 25 μM;<br>D: >25 μM | Avg Activity (LACV)<br>A: EC50 ≤ 1 μM;<br>B: 1 < EC50 ≤ 10 μM;<br>C: 10 < EC50 ≤ 25 μM;<br>D: >25 μM | Avg Activity (*C. Caviae*)<br>A: EC50 ≤ 1 μM;<br>B: 1 < EC50 ≤ 10 μM;<br>C: 10 < EC50 ≤ 25 μM;<br>D: >25 μM;<br>n.d.: not determined | Misc Virus Activity<br>A: EC50 ≤ 1 μM;<br>B: 1 < EC50 ≤ 10 μM;<br>C: 10 < EC50 ≤ 25 μM;<br>D: >25 μM;<br>n.d.: not determined |
|---|---|---|---|---|
| 40 | A | A | A | Dengue: A<br>Tacaribe: A<br>Influenza: A<br>Ebola: C<br>MPX: n.d.<br>Rift Valley Fever: A<br>Lymphocytic<br>Choriomeningitis: A<br>(reduces yield >$10^4$-fold) |
| 42 | A | A | A | n.d. |
| 44 | A | A | A | n.d. |
| 45 | A | B | A | Dengue: A<br>Tacaribe: A<br>Influenza: A<br>Ebola: n.d.<br>MPX: n.d. |
| 47 | B | A | A | n.d. |
| 48 | B | A | A | Dengue: A<br>Tacaribe: A<br>Influenza: B<br>Ebola: n.d.<br>MPX: n.d. |
| 49 | B | A | B | Data for HCl salt<br>Dengue: A<br>Tacaribe: A<br>Influenza: A<br>Ebola: n.d.<br>MPX: n.d. |
| 50 | B | B | A | n.d. |
| 51 | B | B | A | n.d. |
| 52 | B | B | A | n.d. |
| 53 | B | B | A | n.d. |
| 54 | B | B | A | n.d. |
| 55 | B | B | A | n.d. |
| 56 | B | B | A | n.d. |
| 57 | B | B | A | n.d. |
| 58 | B | B | A | n.d. |
| 59 | B | B | A | n.d. |
| 60 | B | B | A | n.d. |
| 61 | B | B | B | n.d. |
| 62 | B | B | B | n.d. |
| 63 | B | B | B | n.d. |
| 65 | B | B | B | n.d. |
| 66 | B | D | A | n.d. |
| 67 | B | D | A | n.d. |

TABLE 10-continued

Anti-Viral and Anti-Bacterial Activity of certain compounds of Formula I of the present invention.

| Compound | Avg Activity (VV)<br>A: $EC_{50} \leq 1$ μM;<br>B: $1 < EC_{50} \leq 10$ μM;<br>C: $10 < EC_{50} \leq 25$ μM;<br>D: >25 μM | Avg Activity (LACV)<br>A: EC50 ≤ 1 μM;<br>B: 1 < EC50 ≤ 10 μM;<br>C: 10 < EC50 ≤ 25 μM;<br>D: >25 μM | Avg Activity (*C. Caviae*)<br>A: EC50 ≤ 1 μM;<br>B: 1 < EC50 ≤ 10 μM;<br>C: 10 < EC50 ≤ 25 μM;<br>D: >25 μM;<br>n.d.: not determined | Misc Virus Activity<br>A: EC50 ≤ 1 μM;<br>B: 1 < EC50 ≤ 10 μM;<br>C: 10 < EC50 ≤ 25 μM;<br>D: >25 μM;<br>n.d.: not determined |
|---|---|---|---|---|
| 70 | B | n.d. | n.d. | n.d. |
| 71 | C | D | A | n.d. |

TABLE 11

Anti-Viral and Anti-Bacterial Activity of certain novel compounds of Formula II of the present invention.

| Compound | Avg Activity (VV)<br>A: EC50 ≤ 1 μM;<br>B: 1 < EC50 ≤ 10 μM;<br>C: 10 < EC50 ≤ 25 μM;<br>D: >25 μM | Avg Activity (LACV)<br>A: EC50 ≤ 1 μM;<br>B: 1 < EC50 ≤ 10 μM;<br>C: 10 < EC50 ≤ 25 μM;<br>D: >25 μM<br>n.d.: not determined | Avg Activity (*C. Caviae*)<br>A: EC50 ≤ 1 μM;<br>B: 1 < EC50 ≤ 10 μM;<br>C: 10 < EC50 ≤ 25 μM;<br>D: >25 μM;<br>n.d.: not determined | Misc Activity<br>A: EC50 ≤ 1 μM;<br>B: 1 < EC50 ≤ 10 μM;<br>C: 10 < EC50 ≤ 25 μM;<br>D: >25 μM;<br>n.d.: not determined |
|---|---|---|---|---|
| 2 | A | A | A | n.d. |
| 3 | A | A | A | n.d. |
| 6 | A | A | A | Dengue: A<br>Tacaribe: A<br>Influenza: A<br>Ebola: B<br>MPX: n.d. |
| 7 | A | A | A | n.d. |
| 8 | A | A | A | n.d. |
| 12 | A | D | A | n.d. |
| 23 | B | B | A | n.d. |
| 24 | B | B | A | n.d. |
| 27 | B | D | A | n.d. |
| 28 | B | D | A | n.d. |
| 30 | B | n.d. | A | n.d. |
| 31 | B | n.d. | A | n.d. |
| 32 | C | C | A | n.d. |
| 34 | C | D | B | n.d. |

TABLE 12

Anti-Viral and Anti-Bacterial Activity of certain compounds of Formula II of the present invention.

| Compound | Avg Activity (VV)<br>A: $EC_{50} \leq 1$ μM;<br>B: $1 < EC_{50} \leq 10$ μM;<br>C: $10 < EC_{50} \leq 25$ μM;<br>D: >25 μM; | Avg Activity (LACV)<br>A: EC50 ≤ 1 μM;<br>B: 1 < EC50 ≤ 10 μM;<br>C: 10 < EC50 ≤ 25 μM;<br>D: >25 μM; | Avg Activity (*C. Caviae*)<br>A: EC50 ≤ 1 μM;<br>B: 1 < EC50 ≤ 10 μM;<br>C: 10 < EC50 ≤ 25 μM;<br>D: >25 μM;<br>n.d.: not determined | Misc Virus Activity<br>A: EC50 ≤ 1 μM;<br>B: 1 < EC50 ≤ 10 μM;<br>C: 10 < EC50 ≤ 25 μM;<br>D: >25 μM;<br>n.d.: not determined |
|---|---|---|---|---|
| 39 | A | A | A | Dengue: A<br>Tacaribe: A<br>Influenza: A<br>Ebola: A<br>MPX: n.d.<br>Rift Valley Fever: A<br>Andes: A (reduces yield >100-fold)<br>Sindbis: A<br>Encephalomyocarditis: A<br>Respiratory Syncytial: A<br>Lymphocytic Choriomeningitis: A (reduces yield $>10^4$-fold)<br>HIV-1: A |
| 43 | A | A | A | n.d. |

TABLE 13

Anti-Viral and Anti-Bacterial Activity of certain novel compounds of Formula III of the present invention.

| Compound | Avg Activity (VV) A: EC50 ≤ 1 μM; B: 1 < EC50 ≤ 10 μM; C: 10 < EC50 ≤ 25 μM; D: >25 μM; | Avg Activity (LACV) A: EC50 ≤ 1 μM; B: 1 < EC50 ≤ 10 μM; C: 10 < EC50 ≤ 25 μM; D: >25 μM; n.d.: not determined | Avg Activity (*C. Caviae*) A: EC50 ≤ 1 μM; B: 1 < EC50 ≤ 10 μM; C: 10 < EC50 ≤ 25 μM; D: >25 μM; n.d.: not determined | Misc Activity A: EC50 ≤ 1 μM; B: 1 < EC50 ≤ 10 μM; C: 10 < EC50 ≤ 25 μM; D: >25 μM; n.d.: not determined |
|---|---|---|---|---|
| 9 | A | A | A | n.d. |
| 10 | A | A | B | n.d. |
| 14 | B | A | A | n.d. |

TABLE 14

Anti-Viral and Anti-Bacterial Activity of certain novel compounds of the present invention.

| Compound | Avg Activity (VV) A: EC50 ≤ 1 μM; B: 1 < EC50 ≤ 10 μM; C: 10 < EC50 ≤ 25 μM; D: >25 μM; | Avg Activity (LACV) A: EC50 ≤ 1 μM; B: 1 < EC50 ≤ 10 μM; C: 10 < EC50 ≤ 25 μM; D: >25 μM; n.d.: not determined | Avg Activity (*C. Caviae*) A: EC50 ≤ 1 μM; B: 1 < EC50 ≤ 10 μM; C: 10 < EC50 ≤ 25 μM; D: >25 μM; n.d.: not determined | Misc Activity A: EC50 ≤ 1 μM; B: 1 < EC50 ≤ 10 μM; C: 10 < EC50 ≤ 25 μM; D: >25 μM; n.d.: not determined |
|---|---|---|---|---|
| 16 | B | B | A | n.d. |
| 17 | B | B | A | Dengue: A<br>Tacaribe: A<br>Influenza: A<br>Ebola: n.d.<br>MPX: n.d. |
| 20 | B | B | A | Dengue: A<br>Tacaribe: A<br>Influenza: A<br>Ebola: n.d.<br>MPX: n.d. |
| 25 | B | D | B | n.d. |
| 26 | B | D | C | n.d. |
| 33 | C | D | D | n.d. |
| 35 | C | D | B | n.d. |
| 37 | D | B | n.d. | n.d. |
| 38 | D | B | D | n.d. |

TABLE 15

Anti-Viral and Anti-Bacterial Activity of certain compounds of the present invention.

| Compound | Avg Activity (VV) A: $EC_{50}$ ≤ 1 μM; B: 1 < $EC_{50}$ ≤ 10 μM; C: 10 < $EC_{50}$ ≤ 25 μM; D: >25 μM; | Avg Activity (LACV) A: EC50 ≤ 1 μM; B: 1 < EC50 ≤ 10 μM; C: 10 < EC50 ≤ 25 μM; D: >25 μM; | Avg Activity (*C. Caviae*) A: EC50 ≤ 1 μM; B: 1 < EC50 ≤ 10 μM; C: 10 < EC50 ≤ 25 μM; D: >25 μM; n.d.: not determined | Misc Virus Activity A: EC50 ≤ 1 μM; B: 1 < EC50 ≤ 10 μM; C: 10 < EC50 ≤ 25 μM; D: >25 μM; n.d.: not determined |
|---|---|---|---|---|
| 41 | A | A | A | n.d. |
| 46 | A | B | A | n.d. |
| 64 | B | B | B | n.d. |
| 68 | B | D | B | n.d. |
| 69 | B | D | D | n.d. |
| 72 | C | D | C | n.d. |
| 73 | C | D | D | n.d. |
| 74 | D | B | D | n.d. |

The invention has been described in terms of preferred embodiments thereof, but is more broadly applicable as will be understood by those skilled in the art. The scope of the invention is only limited by the following claims.

What is claimed is:

1. A method for the treatment of a viral or bacterial infection or disease associated therewith wherein the viral infection is caused by a virus family selected from the group consisting of: Bunyaviridae, Poxviridae, Arenaviridae, Picornaviridae, Togaviridae, Flaviviridae, Filoviridae, Paramyxoviridae, Orthomyxoviridae and Retroviridae, comprising administering in a therapeutically effective amount to a mammal in need thereof, a compound of Formula II below or a pharmaceutically acceptable salt thereof:

Formula II

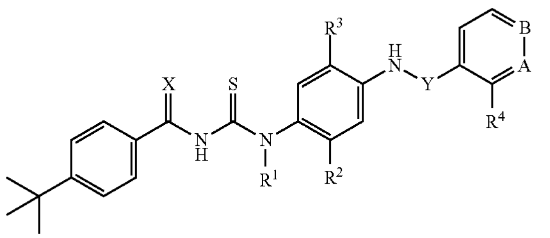

wherein X is selected from the group consisting of oxygen and NH;

Y is selected from the group consisting of: —$CH_2$—, —C(═O)—, —C(═S)— and —C(═NH)—;

A is selected from the group consisting of: N and $CR^5$;

B is selected from the group consisting of: N and $CR^6$;

$R^1$ is selected from the group consisting of: hydrogen and ethyl;

$R^2$ is selected from the group consisting of: hydrogen and chloro;

$R^3$ is selected from the group consisting of: hydrogen, methoxy, amino and hydroxyl;

$R^4$ is selected from the group consisting of: hydrogen, chloro and amino;

$R^5$ is selected from the group consisting of hydrogen and aminomethyl; and $R^6$ is selected from the group consisting of hydrogen, amino and aminomethyl.

2. The method of claim 1, wherein X is oxygen.

3. The method of claim 1, wherein Y is —$CH_2$—.

4. The method of claim 1, wherein Y is —C(═O)—.

5. The method of claim 1, wherein A is C—H.

6. The method of claim 1, wherein B is C—H.

7. The method of claim 1, wherein $R^1$ is hydrogen.

8. The method of claim 1, wherein $R^2$ is hydrogen.

9. The method of claim 1, wherein $R^3$ is methoxy.

10. The method of claim 1, wherein $R^4$ is chloro.

11. The method of claim 1, wherein each of $R^5$ and $R^6$ is hydrogen.

12. The method of claim 1, wherein the compound of Formula II is selected from the group consisting of: N-[4-[(4-tert-butylbenzoyl)-carbamothioylamino]-2-hydroxy-phenyl]-2-chloro-benzamide; 4-tert-butyl-N-[[4-[(2-chloro-phenyl)-methylamino]-3-methoxy-phenyl]-carbamothioyl]-benzamide; N-[2-amino-4-[(4-tert-butylbenzoyl)-carbamothioylamino]-phenyl]-2-chloro-benzamide hydrochloride; N-[(4-benzamido-2-chloro-phenyl)carbamothioyl]-4-tert-butyl-benzamide; 4-tert-butyl-N-[[4-[(2-chlorobenzene-carbothioyl)amino]-3-methoxy-phenyl]-carbamothioyl]benzamide; 4-(aminomethyl)-N-[4-[(4-tert-butylbenzoyl)-carbamothioylamino]-2-methoxy-phenyl] benzamide hydrochloride; N-[4-[(4-tert-butylbenzene-carboximidoyl) -carbamothioylamino]-2-methoxy-phenyl]-2-chloro-benzamide; 4-tert-butyl-N-[[4-[(2-chlorobenzene-carboximidoyl)amino]-3-methoxy-phenyl]-carbamothioyl] benzamide; 3-(aminomethyl)-N-[4-[(4-tert-butylbenzoyl)-carbamothioylamino]-2-methoxy-phenyl]benzamide hydrochloride; 2-amino-N-[4-[(4-tert-butylbenzoyl)-carbamothioylamino]-2-methoxy-phenyl]benzamide; N-[4-[(4-tert-butylbenzoyl)-carbamothioylamino]-2-methoxy-phenyl]pyridine-3-carboxamide; N-[4-[(4-tert-butylbenzoyl)-carbamothioylamino]-2-methoxy-phenyl]pyridine-4-carboxamide; N-[[4-[(4-aminobenzoyl)amino]-3-methoxy-phenyl]-carbamothioyl]-4-tert-butyl-benzamide hydrochloride; N-[4-[(4-tert-butylbenzoyl) -carbamothioyl-ethyl-amino]-2-methoxy-phenyl]-2-chloro-benzamide; N-[4-[(4-tert -butylbenzoyl)-carbamothioylamino]-2-methoxy-phenyl]-2-chloro-benzamide; and N-[(4-benzamidophenyl)-carbamothioyl]-4-tert-butyl-benzamide.

13. The method of claim 12, wherein the compound of Formula II is N-[2-amino-4-[(4-tert-butylbenzoyl)-carbamothioylamino]-phenyl]-2-chloro-benzamide hydrochloride.

14. The method of claim 1, wherein the mammal is a human.

15. The method of claim 1, wherein said Bunyaviridae is selected from the group consisting of Rift Valley fever virus, La Crosse virus and Andes virus.

16. The method of claim 1, wherein said Poxviridae is selected from the vaccinia virus and monkeypox virus.

17. The method of claim 1, wherein said Arenaviridae is selected from the group consisting of Tacaribe virus and lymphocytic choriomeningitis virus.

18. The method of claim 1, wherein said Picornaviridae is Encephalomyocarditis virus.

19. The method of claim 1, wherein said Togaviridae is Sindbis virus.

20. The method of claim 1, wherein said Flaviviridae is Dengue virus.

21. The method of claim 1, wherein the viral infection is caused by a Filoviridae and said Filoviridae is Ebola virus.

22. The method of claim 1, wherein said Orthomyxoviridae is an influenza virus.

23. The method of claim 22, wherein said influenza virus is H1N1 virus.

24. The method of claim 1, wherein said Retroviridae is a Human Immunodeficiency virus.

25. The method of claim 1, which further comprises co-administration of at least one agent selected from the group consisting of antiviral agent, vaccine, and interferon.

26. The method of claim 25, wherein said antiviral agent is Ribavirin.

27. The method of claim 25, wherein said antiviral agent is cidofovir.

28. The method of claim 25, wherein said interferon is pegylated.

29. The method of claim 1, wherein said bacterial infection is caused by a bacteria family selected from the group consisting of Chlamydiaceae and Coxiellaceae.

30. The method of claim 29, wherein said Chlamydiaceae is selected from the group consisting of *Chlamydophila caviae* and *Chlamydophila muridarum*.

31. The method of claim 29, wherein said Coxiellaceae is *Coxiella burnetti*.

32. The method of claim 1, wherein the compound of Formula II is N-[4-[(4-tert -butylbenzoyl)-carbamothioylamino]-2-methoxy-phenyl]-2-chloro-benzamide.

33. The method of claim 32, wherein the viral infection is Ebola virus.

* * * * *